US012612657B2

(12) United States Patent
Yi et al.

(10) Patent No.: US 12,612,657 B2
(45) Date of Patent: Apr. 28, 2026

(54) EXTRACHROMOSOMAL DNA LABELING

(71) Applicant: The Jackson Laboratory, Bar Harbor, ME (US)

(72) Inventors: Eunhee Yi, Bar Harbor, ME (US); Roel Verhaak, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 69 days.

(21) Appl. No.: 16/992,815

(22) Filed: Aug. 13, 2020

(65) Prior Publication Data

US 2021/0062250 A1 Mar. 4, 2021

Related U.S. Application Data

(60) Provisional application No. 62/887,931, filed on Aug. 16, 2019.

(51) Int. Cl.
*C12N 9/22* (2006.01)
*C12N 15/11* (2006.01)
*C12Q 1/6841* (2018.01)

(52) U.S. Cl.
CPC ............. *C12Q 1/6841* (2013.01); *C12N 9/22* (2013.01); *C12N 15/11* (2013.01); *C12N 2310/20* (2017.05)

(58) Field of Classification Search
CPC ............ C12Q 1/6816; C12Q 2521/301; C12Q 2563/107; C12Q 2565/601
See application file for complete search history.

(56) References Cited

U.S. PATENT DOCUMENTS

| | | | |
|---|---|---|---|
| 7,078,387 B1 | 7/2006 | Leiden et al. | |
| 2018/0355416 A1* | 12/2018 | Mischel | ............... C12Q 1/6841 |
| 2022/0333172 A1 | 10/2022 | Cheng et al. | |

FOREIGN PATENT DOCUMENTS

| | | |
|---|---|---|
| WO | 1993003769 A1 | 3/1993 |
| WO | 1993009239 A1 | 5/1993 |
| WO | 1993019191 A1 | 9/1993 |
| WO | 1994012649 A2 | 6/1994 |
| WO | 1994028938 A1 | 1/1995 |
| WO | 1995000655 A1 | 1/1995 |
| WO | 1995011984 A2 | 5/1995 |
| WO | 2011160052 A2 | 12/2011 |
| WO | 2013176772 A1 | 11/2013 |
| WO | 2016148994 A1 | 9/2016 |

OTHER PUBLICATIONS

Cheng et al., Casilio: a versatile CRISPR-Cas9-Pumilio hybrid for gene regulation and genomic labeling. Cell Research (2016), 26: 254-257 (Year: 2016).*

Yi and Verhaak, Abstract 2564: Tracing extrachromosomal DNA inheritance patterns in glioblastoma using CRISPR. Cancer Res (2019) 79 (13_Supplement): 2564 (Year: 2019).*
DeCarvalho et al., Discordant inheritance of chromosomal and extrachromosomal DNA elements contributes to dynamic disease evolution in glioblastoma. Nat Genet. (2018) 50(5): 708-717 (Year: 2018).*
Chen et al., Dynamic Imaging of Genomic Loci in Living Human Cells by an Optimized CRISPR/Cas System. Cell (2013), 155: 1479-1491 (Year: 2013).*
Qin et al., Live cell imaging of low- and non-repetitive chromosome loci using CRISPR-Cas9. Nature Communications (2017), 8: 14725 (Year: 2017).*
Ma et al., CRISPR-Sirius: RNA scaffolds for signal amplification in genome imaging. Nature Methods (2018), 15: 928-931 (Year: 2018).*
Mao et al., CRISPR/dual-FRET molecular beacon for sensitive live-cell imaging of non-repetitive genomic loci. Nucleic Acids Research (2019), 47(20), e131 (Year: 2019).*
Verhaak et al., Extrachromosomal oncogene amplification in tumour pathogenesis and evolution. Nature Reviews (2019), 19: 283-288 (Year: 2019).*
Kanda et al., Histone-GFP fusion protein enables sensitive analysis of chromosome dynamics in living mammalian cells. Current Biology (1998), 8: 377-385 (Year: 1998).*
Kanda et al., Mitotic segregation of viral and cellular acentric extrachromosomal molecules by chromosome tethering. Journal of Cell Science (2000), 114: 49-58 (Year: 2000).*
Maass et al., Spatiotemporal allele organization by allele-specific CRISPR live-cell imaging (SNP-CLING). Nature Structural and Molecular Biology (2018), 25: 176-184 (Year: 2018).*
Cheong and Hall, Engineering RNA sequence specificity of Pumilio repeats. PNAS (2006), 103: 13635-13639 (Year: 2006).*
Wu et al., Progress and challenges for live-cell imaging of genomic loci using CRISPR-based platforms. Genomics Proteomics Bioinformatics (2019), 17: 119-128 (Year: 2019).*
Chaudhary et al., Visualizing live chromatin dynamics through CRISPR-based imaging techniques. Molecules and Cells (2021), 44: 627-636 (Year: 2021).*
Cheng et al., Casilio: a versatile CRISPR-Cas9-Pumilio hybrid for gene regulation and genomic labeling. Cell Res. Feb. 2016;26(2):254-7. doi: 10.1038/cr.2016.3. Epub Jan. 15, 2016.
Filipovska et al., A universal code for RNA recognition by PUF proteins. Nat Chem Biol. May 15, 2011;7(7):425-7. doi: 10.1038/nchembio.577.
National Human Genome Research Institute, "Telomere", updated Jun. 7, 2023, https://www.genome.gov/genetics-glossary/Telomere#:~:text=A%20telomere%20is%20a%20region,successfully%2C%20and%20the%20cell%20dies, accessed Jun. 12, 2023.
National Human Genome Research Institute, "Centromere", updated Jun. 7, 2023, https://www.genome.gov/genetics-glossary/Centromere, accessed Jun. 12, 2023.

(Continued)

*Primary Examiner* — Catherine Konopka

(74) *Attorney, Agent, or Firm* — McDonnell Boehnen Hulbert & Berghoff LLP

(57) ABSTRACT

Provided herein are methods and tools for targeting detecting (e.g., imaging) extrachromosomal DNA, for example, in cancer cells.

9 Claims, 23 Drawing Sheets

Specification includes a Sequence Listing.

(56) References Cited

OTHER PUBLICATIONS

Abil et al. "Modular assembly of designer PUF proteins for specific post-transcriptional regulation of endogenous RNA". Journal of Biological Engineering 8:7, (2014).

Ali et al. "Gene transfer into the mouse retina mediated by an adeno-associated viral vector". Hum Mol Genet. May 1996;5(5):591-4.

Ali et al. "Adeno-associated virus gene transfer to mouse retina". Hum Gene Ther. 1998;9:81-86.

Bennett et al. "Real-time, noninvasive in vivo assessment of Adeno-asoociated virus-mediated retinal transduction". Invest Ophthalmol Vis Sci. 1997;38:2857-2863.

Bitter et al. "Expression and secretion vectors for yeast". Methods Enzymol. 1987;153:516-44.

Boch et al. "Xanthomonas AvrBs3 Family-Type III Effectors: Discovery and Function". Annual Review of Phytopathology 48: 419-36, (2010).

Boch. "TALEs of genome targeting". Nat Biotechnol. 29(2): 135-136, (Feb. 2011).

Borras et al. "Adenoviral reporter gene transfer to the human trabecular meshwork does not alter aqueous humor butflow. Relevance for potential gene therapy of glaucoma". Gene Ther. 6(4):515-24, (Apr. 1999).

Cermak et al. "Efficient design and assembly of custom TALEN and other TAL effector-based constructs for DNA targeting". Nucleic Acids Res. 39(12): e82, (Apr. 2011).

Cheng et al. "CRISPR-mediated multiplexed live cell imaging of non-repetitive genomic loci with one guide RNA per locus". Nature 13(1):1871, (2022).

Christian et al. "Targeting DNA double-strand breaks with TAL effector nucleases". Genetics 186(2): 757-761, (Jul. 2010).

Flannery et al. "Efficient photoreceptor-targeted gene expression in vivo by recombinant adeno-associated virus". Proc Natl Acad Sci U S A. Jun. 24, 1997;94(13):6916-21.

Flotte et al. "Stable in vivo expression of the cystic fibrosis transmembrane conductance regulator with an adeno-associated virus vector". Proc Natl Acad Sci U S A. Nov. 15, 1993;90(22):10613-7.

Gabsalilow et al. "Site- and strand-specific nicking of DNA by fusion proteins derived from MutH and I-Scel or TALE repeats". Nucleic Acids Res. 41(7): e83, (Feb. 2013).

Harrington et al. "Programmed DNA destruction by miniature CRISPR-Cas14 enzymes". Science 362(6416): 839-842, (Oct. 2018).

Jomary et al. "Rescue of photoreceptor function by AAV-mediated gene transfer in a mouse model of inherited retinal degeneration". Gene Ther. Jul. 1997;4(7):683-90.

Juillerat et al. "Optimized tuning of TALEN specificity using non-conventional RVDs". Sci Rep. 5: 8150, (Jan. 2015).

Kim et al. "Hybrid restriction enzymes: zinc finger fusions to Fok I cleavage domain". Proc Natl Acad Sci U S A. Feb. 6, 1996; 93(3): 1156-1160.

Li et al. "In vivo transfer of a reporter gene to the retina mediated by an adenoviral vector". Invest Ophthalmol Vis Sci. 35(5): 2543-9, (Apr. 1994).

Li et al. "Phenotype correction in retinal pigment epithelium in murine mucopolysaccharidosis VII by adenovirus-mediated gene transfer". Proc Natl Acad Sci U S A. Aug. 15, 1995; 92(17): 7700-7704.

Mendelson et al. "Expression and rescue of a nonselected marker from an integrated AAV vector". Virology. Sep. 1988;166(1):154-65.

Miyoshi et al. "Stable and efficient gene transfer into the retina using an HIV-based lentiviral vector". Proc Natl Acad Sci U S A. Sep. 16, 1997;94(19):10319-23.

Moscou et al. "A simple cipher governs DNA recognition by TAL effectors". Science 326 (5959): 1501, (Dec. 2009).

Panyam et al. "Biodegradable nanoparticles for drug and gene delivery to cells and tissue". Adv Drug Deliv Rev. 55(3): 329-347, (Feb. 2003).

Ramirez et al. "Engineered zinc finger nickases induce homology-directed repair with reduced mutagenic effects". Nucleic Acids Research 40(12): 5560-5568, (Feb. 2012).

Rolling et al. "Evaluation of adeno-associated virus-mediated gene transfer into the rat retina by clinical fluorescence photography". Hum. Gene Ther. 1999, 10: 641-648.

Sakamoto et al. "A vitrectomy improves the transfection efficiency of adenoviral vector-mediated gene transfer to Müller cells". Gene Ther. Aug. 1998;5(8):1088-97.

Samulski et al. "Helper-free stocks of recombinant adeno-associated viruses: normal integration does not require viral gene expression". J Virol. Sep. 1989;63(9):3822-8.

Takahashi et al. "Rescue from Photoreceptor Degeneration in therd Mouse by Human Immunodeficiency Virus Vector-Mediated Gene Transfer". J Virol. Sep. 1999;73(9):7812-6.

Tam et al. "The Puf family of RNA-binding proteins in plants: phylogeny, structural modeling, activity and subcellular localization". BMC Plant Biology 10: 44, (2010).

Turner et al. "Extrachromosomal oncogene amplification drives tumour evolution and genetic heterogeneity". Nature 543(7643): 122-135, (Mar. 2017).

Lower et al. "Special Issue: Repetitive DNA Sequences". Genes (Basel) 10(11):896, (2019).

Qin et al. "Live cell imaging of low- and non-repetitive chromosome loci using CRISPR-Cas9", Nature Communications 8: 14725, (2017).

Pedelacq et al., "Engineering and characterization of a superfolder green fluorescent protein", Nat. Biotechnol. 24: 79-88, 2005.

* cited by examiner

HF3016 (p14) – BP02-positive metaphase cell (BP02+BAC+)

SEQUENCE LISTING

<160> NUMBER OF SEQ ID NOS: 25

<210> SEQ ID NO 1
<211> LENGTH: 349
<212> TYPE: PRT
<213> ORGANISM: Homo sapiens

<400> SEQUENCE: 1

-continued

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
            85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
            115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
            165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
            195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
            245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
            275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
            325                 330                 335

Leu Glu Lys Tyr Tyr Met Lys Asn Gly Val Asp Leu Gly
            340                 345
```

```
<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tactaaaccc tgattatgat                                    20
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tggctcatca tgaggcactt                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
aagagtgtca ttccatcctg                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tttgtggcac tctcccagga                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
atatctatac ctattacaca                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgtttcctac tgaagaattg                                                  20

<210> SEQ ID NO 8
<211> LENGTH: 20
<212> TYPE: RNA
<213> ORGANISM: Artificial Sequence
<220> FEATURE:
<223> OTHER INFORMATION: Synthetic

<400> SEQUENCE: 8
uacuaaaccc ugauuaugau                                                  20

<210> SEQ ID NO 9
<211> LENGTH: 20
<212> TYPE: RNA
<213> ORGANISM: Artificial Sequence
<220> FEATURE:
<223> OTHER INFORMATION: Synthetic
```

-continued

```
<400> SEQUENCE: 9
uggcucauca ugaggcacuu                                           20

<210> SEQ ID NO 10
<211> LENGTH: 20
<212> TYPE: RNA
<213> ORGANISM: Artificial Sequence
<220> FEATURE:
<223> OTHER INFORMATION: Synthetic

<400> SEQUENCE: 10
aagaguguca uuccauccug                                           20

<210> SEQ ID NO 11
<211> LENGTH: 20
<212> TYPE: RNA
<213> ORGANISM: Artificial Sequence
<220> FEATURE:
<223> OTHER INFORMATION: Synthetic

<400> SEQUENCE: 11
uuuguggcac ucucccagga                                           20

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12
auaucuauac cuauuacaca                                           20

<210> SEQ ID NO 13
<211> LENGTH: 20
<212> TYPE: RNA
<213> ORGANISM: Artificial Sequence
<220> FEATURE:
<223> OTHER INFORMATION: Synthetic

<400> SEQUENCE: 13
uguuuccuac ugaagaauug                                           20

<210> SEQ ID NO 14
<211> LENGTH: 80
<212> TYPE: DNA
<213> ORGANISM: Artificial Sequence
<220> FEATURE:
<223> OTHER INFORMATION: Synthetic

<400> SEQUENCE: 14
aagtttcacc taatctctta aaaaataccg tactaaaccc tgattatgat caagtaaaca    60
tcactgcact tggaccagcc                                           80

<210> SEQ ID NO 15
<211> LENGTH: 80
<212> TYPE: DNA
<213> ORGANISM: Artificial Sequence
<220> FEATURE:
<223> OTHER INFORMATION: Synthetic

<400> SEQUENCE: 15
ggctggtcca agtgcagtga tgtttacttg atcataatca gggtttagta cggtattttt    60
taagagatta ggtgaaactt                                           80
```

-continued

```
<210> SEQ ID NO 16
<211> LENGTH: 80
<212> TYPE: DNA
<213> ORGANISM: Artificial Sequence
<220> FEATURE:
<223> OTHER INFORMATION: Synthetic

<400> SEQUENCE: 16
agtgaactga gacaagctgc ctcagccccc tggctcatca tgaggcactt cacacggatt      60
gctcattaag aaaatgcaaa                                                  80

<210> SEQ ID NO 17
<211> LENGTH: 80
<212> TYPE: DNA
<213> ORGANISM: Artificial Sequence
<220> FEATURE:
<223> OTHER INFORMATION: Synthetic

<400> SEQUENCE: 17
tttgcatttt cttaatgagc aatccgtgtg aagtgcctca tgatgagcca gggggctgag      60
gcagcttgtc tcagttcact                                                  80

<210> SEQ ID NO 18
<211> LENGTH: 80
<212> TYPE: DNA
<213> ORGANISM: Artificial Sequence
<220> FEATURE:
<223> OTHER INFORMATION: Synthetic

<400> SEQUENCE: 18
gctatttaag actacacttt ctgaatgcca aagagtgtca ttccatcctg acagcagttc      60
ctttgtggct ttgctcaaac                                                  80

<210> SEQ ID NO 19
<211> LENGTH: 80
<212> TYPE: DNA
<213> ORGANISM: Artificial Sequence
<220> FEATURE:
<223> OTHER INFORMATION: Synthetic

<400> SEQUENCE: 19
gtttgagcaa agccacaaag gaactgctgt caggatggaa tgacactctt tggcattcag      60
aaagtgtagt cttaaatagc                                                  80

<210> SEQ ID NO 20
<211> LENGTH: 80
<212> TYPE: DNA
<213> ORGANISM: Artificial Sequence
<220> FEATURE:
<223> OTHER INFORMATION: Synthetic

<400> SEQUENCE: 20
aagaagtgct gttcctttaa actttgcccc tttgtggcac tctcccagga ggaaaatctt      60
aggccctccc tcccatgagg                                                  80

<210> SEQ ID NO 21
<211> LENGTH: 80
<212> TYPE: DNA
<213> ORGANISM: Artificial Sequence
<220> FEATURE:
<223> OTHER INFORMATION: Synthetic
```

-continued

```
<400> SEQUENCE: 21
cctcatggga gggagggcct aagattttcc tcctgggaga gtgccacaaa ggggcaaagt      60
ttaaaggaac agcacttctt                                                  80

<210> SEQ ID NO 22
<211> LENGTH: 80
<212> TYPE: DNA
<213> ORGANISM: Artificial Sequence
<220> FEATURE:
<223> OTHER INFORMATION: Synthetic

<400> SEQUENCE: 22
ttataaatat catgattact accatttcaa atatctatac ctattacaca tggttttctt      60
gttaattttg aacgtggcgg                                                  80

<210> SEQ ID NO 23
<211> LENGTH: 80
<212> TYPE: DNA
<213> ORGANISM: Artificial Sequence
<220> FEATURE:
<223> OTHER INFORMATION: Synthetic

<400> SEQUENCE: 23
ccgccacgtt caaaattaac aagaaaacca tgtgtaatag gtatagatat ttgaaatggt      60
agtaatcatg atatttataa                                                  80

<210> SEQ ID NO 24
<211> LENGTH: 80
<212> TYPE: DNA
<213> ORGANISM: Artificial Sequence
<220> FEATURE:
<223> OTHER INFORMATION: Synthetic

<400> SEQUENCE: 24
gacatctgga gagggagaga ggaattacca tgtttcctac tgaagaattg ctttataagt      60
tgataaggcc cctttaaaac                                                  80

<210> SEQ ID NO 25
<211> LENGTH: 80
<212> TYPE: DNA
<213> ORGANISM: Artificial Sequence
<220> FEATURE:
<223> OTHER INFORMATION: Synthetic

<400> SEQUENCE: 25
gttttaaagg ggccttatca acttataaag caattcttca gtaggaaaca tggtaattcc      60
tctctccctc tccagatgtc                                                  80
```

EXTRACHROMOSOMAL DNA LABELING

RELATED APPLICATION

This application claims the benefit under 35 U.S.C. § 119(e) of U.S. provisional application Ser. No. 62/887,931, filed Aug. 16, 2019, which is herein incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 27, 2020, is named J022770072US01-SEQ-HJD and is 8 kilobytes in size.

BACKGROUND

Extrachromosomal DNAs are small, circular, gene-carrying DNA fragments that occur in cancer cells. Extrachromosomal DNA (ecDNA) may contain extra copies of genes that promote cancer growth or genes that make cells resistant to cancer treatments. As such, ecDNA is a likely source of treatment failure and cancer recurrence.

SUMMARY

Provided herein, in some aspects, are methods and tools that enable the targeting and/or detection (e.g., visualization) of extrachromosomal DNA (ecDNA) within cancer cells, on the basis of genetic sequences within ecDNA that do not exist in chromosomal DNA. These sequences enable targeting of, for example, fluorescent proteins and/or effector proteins (e.g., nucleases) to the ecDNA using genetic approaches. These sequences within ecDNA may also be mutated or cleaved to inhibit the expression or activity of a gene (e.g., an oncogene). The experimental data provided herein show that the methods and tools of the present disclosure can be used to proficiently and selectively target ecDNA, for example, to label and validate the location and amount of ecDNA within cancer cells, such as glioblastoma cells, melanoma cells, sarcoma cells, bladder cancer cells, and/or esophageal cancer cells. The experimental data provided herein also demonstrate that ecDNA can be transferred between cells from different patients, which suggests that ecDNA may be a driver of tumor evolution and treatment resistance. Some aspects of the present disclosure provide cells that comprise extrachromosomal deoxyribonucleic acid (ecDNA) that has been bound at a breakpoint junction by a catalytically-inactive RNA-guided nuclease complexed with a guide RNA (gRNA) linked to a detectable molecule. In some embodiments, the gRNA comprises (a) a targeting sequence that is complementary to the breakpoint junction, (b) a RNA-guided nuclease-binding sequence, and (c) a Pumilio-FBF (PUF) domain binding sequence (PBS). In some embodiments, the cell further comprises a PUF domain linked to the detectable molecule, and the PUF domain binds to the PBS. In some embodiments, the cell comprises multiple PUF domains linked to multiple detectable molecules, and the PUF domains bind to the PBS.

In some embodiments, the catalytically-inactive RNA-guided nuclease is dCas9.

Other aspects of the present disclosure provide cells comprising extrachromosomal deoxyribonucleic acid (ecDNA) that have been genetically modified at a breakpoint junction to express a detectable molecule.

In some embodiments, the programmable nuclease-based gene editing system comprises (a) a RNA-guided nuclease or a nucleic acid encoding an RNA-guided nuclease, (b) a guide RNA (gRNA) comprising a RNA-guided nuclease-binding sequence and a targeting sequence that is complementary to the breakpoint junction, and (c) a donor nucleic acid comprising a coding region that encodes the detectable molecule, wherein the coding region is flanked by homology arms that are complementary to sequences of the breakpoint junction. In some embodiments, the RNA-guided nuclease is a Cas9 nuclease.

In some embodiments, the programmable nuclease-based gene editing system comprises (a) a zinc-finger nuclease (ZFN) or a nucleic acid encoding a ZFN that binds to the breakpoint junction, and (b) a donor nucleic acid comprising a coding region that encodes the detectable molecule, wherein the coding region is flanked by homology arms that are complementary to sequences of the breakpoint junction.

In some embodiments, the programmable nuclease-based gene editing system comprises (a) a transcription activator-like effector nuclease (TALEN) or a nucleic acid encoding a TALEN, (b) a transcription activator-like effector (TALE) or a nucleic acid encoding a TALE that binds to the breakpoint junction, and (c) a donor nucleic acid comprising a coding region that encodes the detectable molecule, wherein the coding region is flanked by homology arms that are complementary to sequences of the breakpoint junction.

Also provided herein are methods that comprise detecting the detectable molecule of a cell, thereby detecting the ecDNA.

Also provided herein are methods that comprise imaging the detectable molecule of a cell of, thereby imaging the ecDNA.

Further provided herein are compositions comprising a cell of the present disclosure.

Also provided herein are methods of producing a cell of the present disclosure. In some embodiments, the methods comprise introducing into the cell (a) the catalytically-inactive RNA-guided nuclease or a nucleic acid encoding the catalytically-inactive RNA-guided nuclease, (b) a gRNA comprising (i) a targeting sequence that is complementary to the breakpoint junction, (ii) a RNA-guided nuclease-binding sequence, and (iii) Pumilio-FBF (PUF) domain binding sequence (PBS), and (c) a PUF domain linked to the detectable molecule, wherein the PUF domain binds to the PBS. In some embodiments, the methods comprise introducing into the cell the programmable nuclease-based gene editing system of any one of the preceding claims. In some embodiments, the breakpoint junction is genetically modified using a programmable nuclease-based gene editing system.

Also provided herein are molecular cytogenetic tracing methods. In some embodiments, the methods comprise imaging ecDNA in a cell in which the ecDNA has been bound at a breakpoint junction by a catalytically-inactive RNA-guided nuclease complexed with a guide RNA (gRNA) linked to a detectable molecule. In some embodiments, the methods comprise imaging ecDNA in a cell in which the ecDNA that has been genetically modified at a breakpoint junction to express a detectable molecule.

Also provided herein are molecular cytogenetic labeling methods. In some embodiments, the methods comprise introducing into a cell comprising ecDNA (a) the catalytically-inactive RNA-guided nuclease, (b) a gRNA comprising (i) a targeting sequence that is complementary to the breakpoint junction, (ii) a RNA-guided nuclease-binding sequence, and (ii) a Pumilio-FBF (PUF) domain binding sequence (PBS), and (c) a PUF domain linked to the detectable molecule, wherein the PUF domain binds to the PBS. In some embodiments, the methods comprise introducing into a cell comprising ecDNA a programmable nuclease-based gene editing system that targets a breakpoint junction in the ecDNA to incorporate a detectable molecule.

In some embodiments, the cell is a cancer cell. In some embodiments, the cancer cell is a glioblastoma cell. In some embodiments, the cell is a melanoma cell. In some embodiments, the cell is a sarcoma cell. In some embodiments, the cell is a bladder cancer cell. In some embodiments, the cell is a esophageal cancer cell.

In some embodiments, the detectable molecule is a fluorescent protein.

Yet other aspects of the present disclosure provide a guide RNA (gRNA) comprising (a) a targeting sequence that is complementary to a breakpoint junction in extrachromosomal DNA and (b) a RNA-guided nuclease-binding sequence. In some embodiments, the gRNA is complexed with a RNA-guided nuclease. In some embodiments, the gRNA further comprises (c) a Pumilio-FBF (PUF) domain binding sequence (PBS).

In some embodiments, the RNA-guided nuclease is a Cas9 nuclease or a catalytically-inactive Cas9 nuclease.

Also provided herein are cells, compositions, and/or kits comprising the gRNA.

BRIEF DESCRIPTION OF THE DRAWINGS

(FIG. 1A) Identification of ecDNA-specific breakpoint junctions. JC=Junction (FIG. 1B) Schematic representation of EDTB version 1. (FIG. 1C) Green fluorescent protein (GFP) is inserted through homology directed repair (HDR). (FIG. 1D) Schematic representation of EDTB version 2. (FIG. 1E) Multiple GFP tagging at the ecDNA breakpoint region.

(FIG. 3A) Strategy of breakpoint validation using PCR. (FIG. 3B) Breakpoint-PCR was performed on the HF3016 and HF3177 glioblastoma neurosphere cell line models (derived from same parent tumor) and PC3 (a negative control prostate cancer line model).

(FIG. 4A) Strategy of breakpoint validation using breakpoint-FISH. (FIG. 4B) Representative image showing breakpoint signals. Yellow dots on the merged image indicate breakpoint signals. (FIG. 4C) Breakpoint signal for each breakpoints were manually counted.

(FIG. 6A) Strategy of a cell-free targeting efficiency test system. (FIG. 6B) Each breakpoint junction was successfully targeted by gRNA that was designed, shown by the cleaved products in the validating PCR assay (third lane for each individual breakpoint).

(FIG. 7A) The components of EDTBv1. (FIG. 7B) EDTBv1 transduction system will be established by measuring GFP signal at the different time points of post-transfection.

(FIG. 8A) The components of EDTBv2. (FIG. 8B) EDTBv2 was transduced into HF3016 and GFP signal was observed after 24-48 hrs post transfection. (FIG. 8C) Targeting efficiency of EDTBv2 was evaluated by manual counting. White arrow: cell without BP06. Red arrow: cell with BP06. (FIG. 8D) Expression level of BP06-related genes were measured by qPCR.

(FIG. 9A) Representative images of EDTBv2-targeted cells on the HF3016, HF3177, and PC3 (top panel). Scale bar, 10 mm. Histograms of targeting efficiency of EDTBv2 (FIG. 9B) Representative two color images of BP-FISH signal (red) and EDTBv2 signal (green). Scale bar, 10 mm. Histograms of colocalized spots (right panel, n>20 cells per condition).

(FIG. 10A) BP-PCR was performed in HF2354 treated with a fresh medium or a collected medium from HF3016 and HF3177 for 48 hrs. (FIG. 10B) BP-FISH was performed in HF2354 treated with a fresh medium or a collected medium from HF3016 and HF3177 for 48 hrs.

DETAILED DESCRIPTION

Figure 1A:
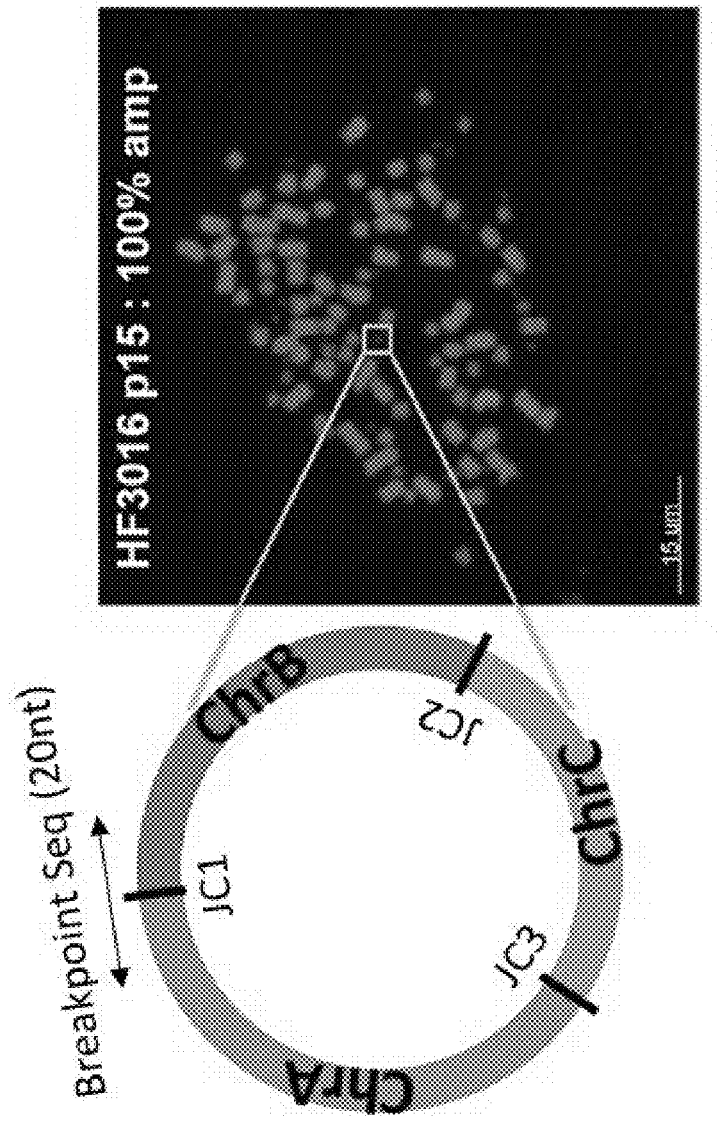
FIGS. 1A-1E. Strategy for ecDNA tracking toolbox (EDTB) development.

The present disclosure provides, in some aspects, are methods and compositions for targeting and/or detecting (e.g., imaging) in cells (e.g., live cells) extrachromosomal DNA (ecDNA) by targeting a (one or more) breakpoint junction. ecDNA is generated by the rearrangement of various chromosomal fragments, resulting in the generation of various "breakpoint junctions" unique to the ecDNA (FIG. 1A). These breakpoint junctions are sequences that flank the point at which two chromosomal fragments join together (FIG. 1A, black arrow). These breakpoint junctions have not been found in autosomal sequences. The technology provided herein, in some embodiments, may be used to specifically target ecDNA, e.g., to label ecDNA with, for example, a detectable molecule (e.g., fluorescent protein, such as green fluorescence protein (GFP)), by targeting one or more breakpoint junction(s) using, for example, a programmable nuclease-based system. Examples of such programmable nuclease-based systems that may be used as provide herein include: RNA-guided nucleases (e.g., Cas9 or catalytically inactive Cas9 (dCas9)) that function cooperatively with a single unique guide RNA (gRNA) to label a breakpoint junction; and other gene editing-based systems that include, for example, transcription activator-like effector nuclease (TALENS) or zinc finger nucleases (ZFNs).

In some embodiments, one of two different versions of a CRISPR-based "ecDNA tracing toolbox (EDTB)" system may be used (FIGS. 1B-1E), examples of which are outlined as follows.

Figure 1B:
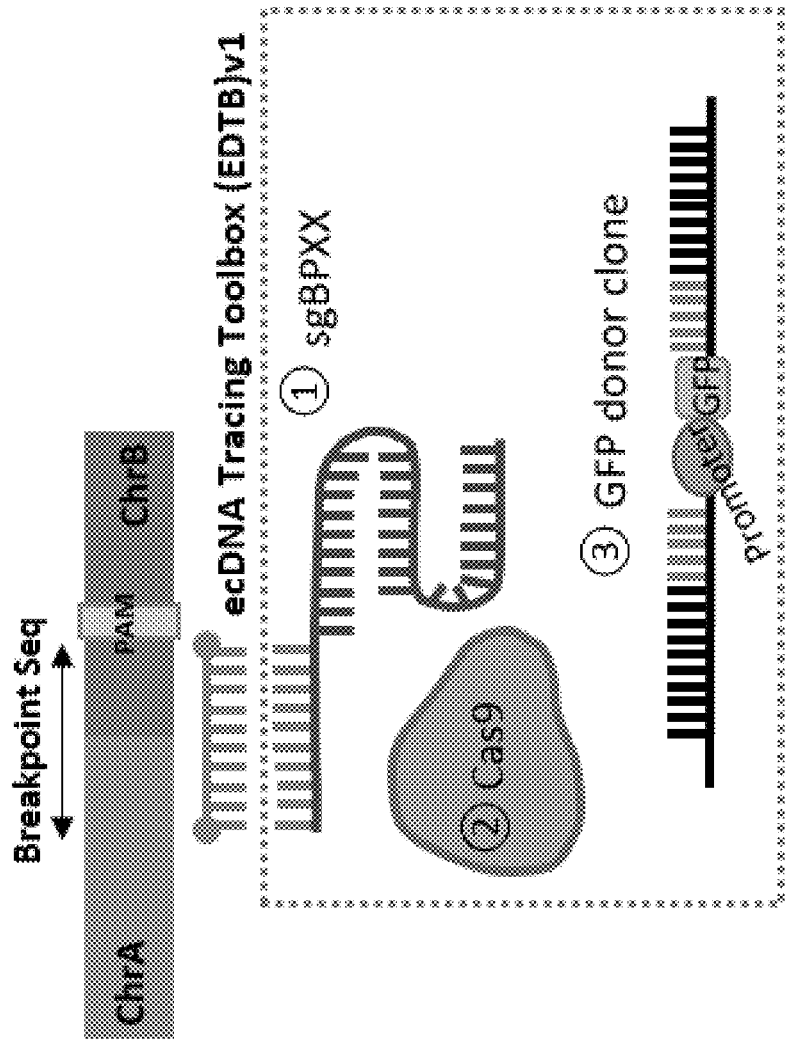
Figure 1C:
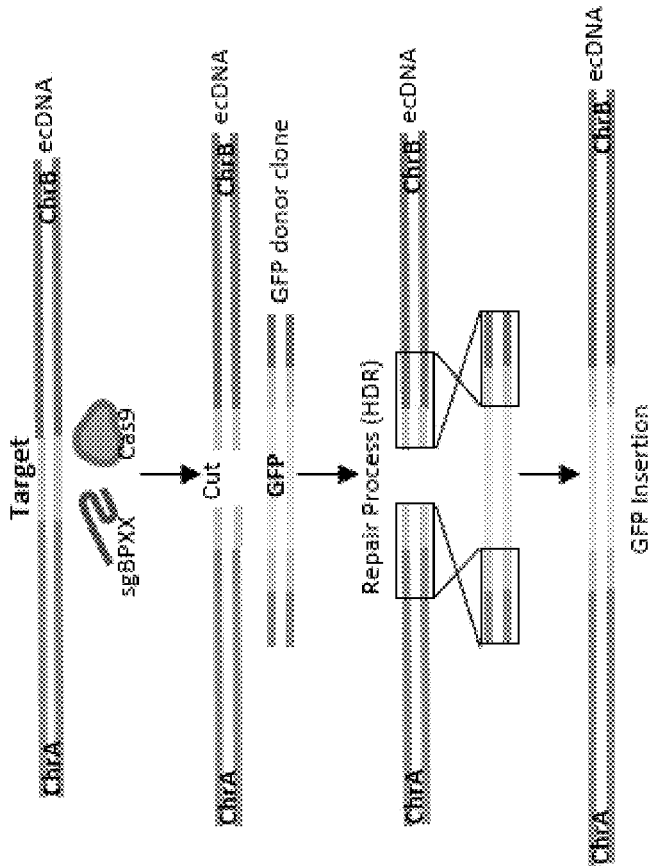
Figure 1D:
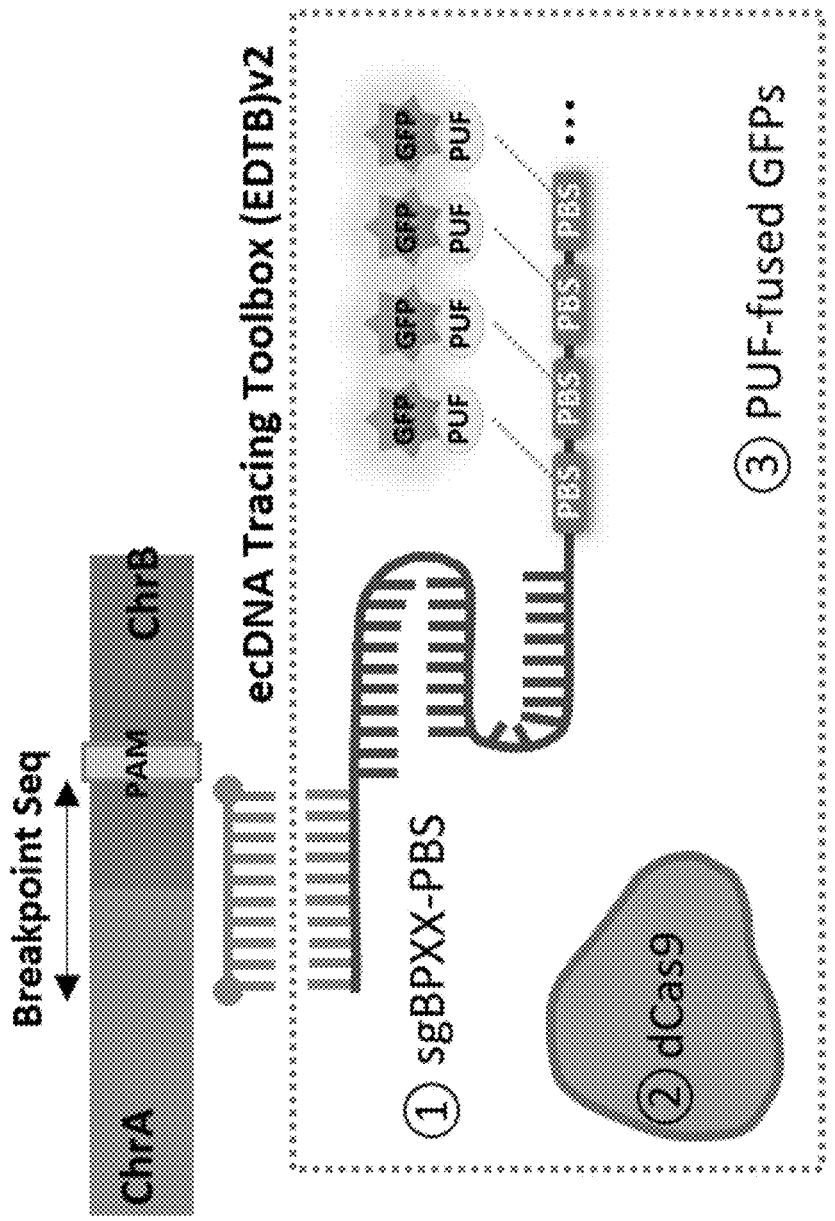

One version of an ecDNA tracing toolbox system (EDTBv2) uses "Casilio" technology (see, e.g., WO 2016/148994, the entire contents of which is incorporated by reference herein). This EDTB version includes (a) a break-point-specific gRNA that includes a spacer sequence (e.g., ~20 nucleotides long) that binds specifically to the breakpoint junction, a region to which a nuclease-deactivated (catalytically inactive) Cas9 (dCas9) binds, and at least one PUF binding site (PBS) (sgBPXX), (b) at least one PUF domain-fused detectable molecule (e.g., fluorescent protein), and (c) dCas9, which is used to secure the detectable molecule at a breakpoint junction of ecDNA (FIG. 1D). This EDTB system transiently labels the breakpoint junction of ecDNA.

Another version of the ecDNA tracing toolbox system (EDTBv1) may be used to insert a detectable protein coding sequence (e.g., a fluorescent protein coding sequence) at a breakpoint junction of ecDNA. This EDTB version may include, for example, a breakpoint junction-specific gRNA, Cas9, and a donor polynucleotide encoding the detectable protein flanked by homology arms complementary to regions flanking the breakpoint junction (FIG. 1B). Cas9 cleaves the breakpoint junction of ecDNA after being guided to the locus by the sgBPXX, and the donor polynucleotide is inserted into the ecDNA through a homology-directed repair (HDR) mechanism (FIG. 1C). This EDTB system stably labels the breakpoint junction of ecDNA.

Detection of Extrachromosomal DNA (ecDNA)

In some aspects, the present disclosure provides compositions and methods for detecting extrachromosomal DNA (ecDNA) in cells, such as live cells. Extrachromosomal DNA is found apart from the chromosomal DNA and occurs in prokaryotic cells, eukaryotic cells, and archaeal cells. Extrachromosomal DNA forms when chromosomal DNA breaks, and fragments of the DNA rearrange and ligate outside of the chromosome either autonomously or with other portions of chromosomal DNA. This rearrangement of fragmented DNA creates a unique breakpoint junction sequence, where the two fragments meet, which is not found in chromosomal DNA. A breakpoint junction is any sequence spanning the location where the two fragments join. Thus, as provided herein, a gRNA (or other programmable binding element, such as a TALE or ZFN) may be designed to target (specifically bind to) any sequence spanning the location where two chromosomal fragments join in an ecDNA. The breakpoint junction, in some embodiments, has a length of at least 10 nucleotides. For example, a breakpoint junction may have a length of at least 20, at least 30, at least 40, at least 50, at least 60, at least 70, at least 80, at least 90, or at least 100 nucleotides. In some embodiments, a breakpoint junction has a length of 10-100, 10-90, 10-80, 10-70, 10-60, 10-50, 10-40, 10-30, or 10-20 nucleotides. In some embodiments, a breakpoint junction has length of 10, 11, 12, 13, 14, 15, 16, 17, 18, 19, 20, 21, 22, 23, 24, or 25 nucleotides.

Because ecDNA is formed from fragmented chromosomes, it is prevalent in cells in which the chromosomal DNA is unwound and accessible (e.g., cells with increased levels of DNA replication and repair). In fact, ecDNA occurs in nearly half of human cancer cells studied and rarely occurs in normal cells (Turner, et al., Nature, 2017, 543: 122-125). The frequency of ecDNA in cancer cells may vary by tumor type (e.g., solid, soft tissue), stage of the disease (e.g., stage 1, stage 2, stage 3, stage 4), and whether the cancer is primary or recurrent. Thus, detection of ecDNA, especially numerous molecules of ecDNA, in a cell may suggest that the cell is a cancer cell. In some embodiments, the methods provided herein may be used to detect ecDNA in a cell and further diagnose the cell as a cancer cell.

ecDNA in cancer cells may contain sequences that promote the survival and proliferation of the cancer cell. For example, ecDNA may contain protein-coding genes that produce oncogenic proteins (e.g., epidermal growth factor receptor, Her2, ras, platelet-derived growth factor receptor) just as with chromosomal DNA. In some instances, ecDNA may contain extra copies of protein-coding genes encoding oncogenic proteins. In some instances, ecDNA may contain non-protein-coding genes that control gene expression in cancer cells (e.g., promoters, enhancers, repressors). Thus, in some embodiments, the methods provided herein may be used to detect and isolate ecDNA from a cancer cell, which may then be sequenced to identify oncogenic sequences.

One cancer in which ecDNA is prevalent and may play a crucial role in resistance to treatment and cancer recurrence is glioblastoma. Glioblastoma is the most lethal brain cancer, with a five-year survival rate of 10% and a poor response to standard radiation and cytotoxic therapy. This may be, in part, because glioblastoma tumor cells differ substantially, within an individual tumor over glioblastoma and between tumors, in the amount and prevalence of ecDNA. The prevalence of ecDNA in glioblastoma cells may contribute to resistance to treatment and cancer recurrence and understanding how ecDNA affects cancer cells may provide insights into how to regulate this process. Thus, some aspects of the present disclosure provide methods for detecting ecDNA in glioblastoma cells. Further, non-limiting examples of cancers in which ecDNA is prevalent and may play a crucial role in resistant to treatment and cancer recurrence are melanoma, sarcoma, bladder cancer, and esophageal cancer. Thus, some aspects of the present disclosure provide methods for detecting ecDNA in melanoma, sarcoma, bladder cancer, esophageal cancer, and other cancers.

In some embodiments, methods of detecting breakpoint junctions may be used to investigate the inheritance of ecDNA among daughter cells during cell division. For example, the methods herein may be used to track whether ecDNA is preferentially inherited by one daughter cell and, if so, if that inheritance contributes to enhanced proliferation in the daughter cell that inherited the ecDNA relative to the daughter cell that did not inherit the ecDNA.

In some embodiments, methods provided herein are used to investigate the production of ecDNA in cancer cells (e.g., glioblastoma cells, melanoma cells, sarcoma cells, bladder cancer cells, and/or esophageal cancer cells). For example, methods of detection provided herein may be used to track the production of new breakpoint junctions bound by detectable molecules in ecDNA. The production of new breakpoint junctions may suggest that production of those particular breakpoints provides a selective advantage to the cancer cells (e.g., glioblastoma cells, melanoma cells, sarcoma cells, bladder cancer cells, and/or esophageal cancer cells).

In some embodiments, methods provided herein may be used to investigate the evolution of ecDNA in cancer cells (e.g., glioblastoma cells, melanoma cells, sarcoma cells, bladder cancer cells, and/or esophageal cancer cells). For example, the methods herein may be used to track the fate of a detectable breakpoint junction over multiple cell cycles. If the breakpoint junction persists, it may provide a selective advantage to the cancer cell that contains the breakpoint, whereas if the breakpoint disappears, it may suggest that the ecDNA containing the breakpoint has either disappeared or has rearranged because the gene was not providing a selective advantage to the cancer cell.

In some aspects, the methods herein comprise labeling a breakpoint junction of ecDNA with a detectable molecule to visualize (e.g., image and/or monitor) the ecDNA a live cell, for example. A detectable molecule is any molecule that may be visualized using, for example, chromogenic and/or fluorescent detection methods. Non-limiting examples of detectable molecules include fluorescent proteins, fluorophores, chromogenic molecules, and dyes. Non-limiting examples of fluorescent proteins include: TagBFP, mTagBFP2, Azurite, EBFP2, mKalamal, Sirius, Sapphire, T-Sapphire (blue/ UV proteins); ECFP, Cerulean, SCFP3A, mTurquoise, mTurquoise2, monomeric Midoriishi-Cyan, TagCFP, and mTFP1 (cyan proteins); EGFP, Emerald, Superfolder GFP, Monomeric Azami Green, TagGFP2, mUKG, mWasabi, Clover, mNeonGreen (green proteins); EYFP, Citrine, Venus, SYFP2, TagYFP (yellow proteins); Monomeric Kusabira-Orange, mKOK, mKO2, mOrange, mOrange2 (orange proteins); mRaspberry, mCherry, mStrawberry, mTangerine, tdTomato, TagRFP, TagRFP-T, mApple, mRuby, mRuby2 (red proteins); mPlum, HcRed-Tandem, mKate2, mNeptune, NirFP (far-red proteins); TagRFP657, IFP1.4, iRFP (near-red proteins); mKeima Red, LSS-mKate1, LSS-mKate2, mBeRFP (long stokes shift proteins); PA-GFP, PAmCherry1, PATagRFP (photoactivatable proteins); Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange (photoconvertible proteins); and Dronpa (photoswitchable protein). Non-limiting examples of fluorphores include: hydroxycoumarin, methoxycoumarin, Alexa fluor, aminocoumarin (blue); Cy2, FAM, Alexa fluor 488, Fluorescein FITC, Alexa fluor 430, Alexa fluor 532, HEX (green); Cy3, TRITC, Alexa fluor 546, Alexa fluor 555, R-phycoerythrin (PE) (yellow); Rhodamine Red-X (orange); Tamara, Cy3.5 581, Rox, Alexa fluor 568, Red 613, Texas Red, Alexa fluor 594, Alexa fluor 633, Allophycocyanin, Cy5, Alexa fluor 660, Cy5.5, TruRed, Alexa fluor 680, and Cy7 (red). Non-limiting examples of dyes include Alcian Blue 8GX, Alcian yellow GXS, Alizarin, Alizarin Red S, Alizarin yellow GG, Alizarin yellow R, Azophloxin, Bismarck brown R, Bismarck brown Y, Brilliant cresyl blue, Chrysoidine R, Chrysoidine Y, Congo red, Crystal violet, Ethyl Green, Fuchsin acid, Gentian violet, Janus green, Lissamine fast yellow, Malachite green, Martius yellow, Meldola blue, Metanil yellow, Methyl orange, Methyl red, Naphthalene black 12B, Naphthol green B, Naphthol yellow S, Orange G, Purpurin, Rose bengal, Sudan II, Titan yellow, Tropaeolin O, Tropaeolin OO, Tropaeolin OOO, Victoria blue 4R, Victoria blue B, Victoria blue R, and Xylene cyanol FF.

Cell imaging (visualization) methods of the present disclosure, in some embodiments, are used to visualize ecDNA in live cells. Imaging may be accomplished by any method known in the art. The method of imaging depends on the detectable molecule. For example, fluorescent microscopy (e.g., confocal fluorescent microscopy) can be used to examine the live cell populations when a fluorescent detectable molecule is used.

In some embodiments, more than one detectable molecule is used to detect ecDNA. When multiple detectable molecules are used, they may be the same or different, relative to one another. For example, green fluorescent protein (GFP) may be the only type of detectable protein used to detect ecDNA in a cell, each molecule of GFP localized to a single locus. Alternatively, multiple different fluorescent proteins may be used (e.g., RFP, GFP, BFP, YFP), each molecule localized to a different locus. Thus, in some embodiments, fluorescent proteins having different excitation wavelengths relative to one another may be used. In some embodiments, 2, 3, 4, 5, 6, 7, 8, 9, or 10 different detectable molecules (e.g., different fluorescent proteins) may be used.

In some aspects, the methods herein comprise imaging a cell that comprises multiple breakpoint junctions in ecDNA.

For example, the methods may be used to detect 2-100, 2-75, 2-50, 2-25, 2-15, 2-10, 5-100, 5-75, 5-50, 5-25, 5-15, 5-10, 10-100, 10-75, 10-50, 10-25, or 10-15 breakpoint junctions in ecDNA. In some embodiments, the methods may be used to detect 2, 3, 4, 5, 6, 7, 8, 9, 10, 11, 12, 13, 14, 15, or more breakpoint junctions in ecDNA. Thus, in some embodiments, the cells are transfected with 2-100, 2-75, 2-50, 2-25, 2-15, 2-10, 5-100, 5-75, 5-50, 5-25, 5-15, 5-10, 10-100, 10-75, 10-50, 10-25, or 10-15 gRNAs (or nucleic acids encoding the gRNAs) or programmable nucleases. For example, the cells may be transfected with 2, 3, 4, 5, 6, 7, 8, 9, 10, 11, 12, 13, 14, 15, or more gRNAs (or nucleic acids encoding the gRNAs).

Casilio for Detecting ecDNA

There are currently no methods for detecting ecDNA in live cells. The detection methods provided herein enable tracking of inherited ecDNA among dividing cancer cells, for example, to determine whether some cancer cells are more likely than others to inherit ecDNA upon cellular division. Detection of ecDNA in cells will also enable an assessment of whether some cancer cells are more likely than others to replicate ecDNA and thus produce additional ecDNA molecules, and how this trend may contribute to carcinogenesis and metastasis of the cancer cells. Additionally, detection of ecDNA in cancer cells will enable tracking of how ecDNA evolves as a cancer progresses (e.g., whether breakpoint junctions persist or disappear, signaling decreased or increased mutagenesis). Thus, the tools provided herein may be used for any of the foregoing applications.

The cells, methods, and other compositions provided herein enable the detection of breakpoint junctions in extrachromosomal DNA (ecDNA) in cells (e.g., live cells). In some embodiments, the breakpoint junction in cells is bound by a complex comprising a catalytically-inactive RNA-guided nuclease and a guide RNA (gRNA) linked to a detectable molecule (see, e.g., See, e.g., Cheng A. et al. *Cell Research* 26, 254-257 (2016) and WO 2016/148994, each of which is incorporated herein by reference in its entirety). The detectable molecule bound to the breakpoint junction may be detected by any appropriate method known in the art (e.g., imaging) to allow for detection of the ecDNA.

Methods provided herein to detect ecDNA in cells comprise, in some embodiments, using (a) a catalytically-inactive RNA-guided nuclease, a gRNA comprising (i) a targeting sequence that is complementary to the breakpoint junction, (ii) a RNA-guided nuclease-binding sequence, and (iii) Pumilio-FBF (PUF) domain binding sequence (PBS), and (b) a detectable molecule (e.g., fluorescent protein) linked to a PUF domain (detectable conjugate), wherein the PUF domain binds the PBS. In a cell, the complex formed by the interaction of the RNA-guided nuclease and the gRNA is guided to a specific breakpoint junction in ecDNA, where the gRNA serves as a docking site for the detectable conjugate. The detectable conjugate, tethered to the breakpoint junction, allows detection of the ecDNA.

The cells, methods, and compositions provided herein further enable tracing of breakpoint junctions in ecDNA by molecular cytogenetics. Molecular cytogenetics refers to the labeling and tracing of ecDNA in cancer cells (e.g., glioblastoma cells, melanoma cells, sarcoma cells, bladder cancer cells, and/or esophageal cancer cells) and normal cells. In some embodiments of molecular cytogenetic tracing, the ecDNA in a cell has been bound at a breakpoint junction by a catalytically-inactive RNA-guided nuclease complexed with a gRNA linked to a detectable molecule.

In some embodiments, the breakpoint junction in ecDNA can be labeled for molecular cytogenetic tracing by introducing into a cell comprising ecDNA (a) a catalytically-inactive RNA-guided nuclease, (b) a gRNA comprising (i) a targeting sequence that is complementary to the breakpoint junction, (ii) a RNA-guided nuclease-binding sequence, and (iii) a Pumilio-FBF (PUF) domain binding sequence (PBS), and (c) a PUF domain linked to a detectable molecule, wherein the PUF domains binds to the PBS. Detection of the detectable molecule following molecular cytogenetic labeling allows for molecular cytogenetic tracing of the breakpoint junction in ecDNA.

Guide RNAs (gRNAs)

It should be understood that "gRNA" refers to a gRNA that binds to only one genomic locus (e.g., one breakpoint junction in ecDNA) within a defined region, e.g., within a 1 kb region. That is, the gRNA is designed to include a DNA-targeting sequence that is complementary to only one other sequence within the defined region. In some embodiments, a gRNA is designed to bind to only one sequence in the entire genome of a cell. Nonetheless, as is known in the art, even though a gRNA is designed to be unique to a particular locus, it may bind "off-target," in some instances.

The RNA-guided nuclease interacts with an engineered guide RNA (gRNA), such as a single gRNA. The single gRNA described herein comprises at least three components: a DNA-targeting sequence, an RNA-guided nuclease-binding sequence, and an RNA-binding protein (RBP) domain-binding sequence. In some embodiments, the three fragments are arranged: DNA-targeting sequence, RNA-guided nuclease-binding sequence, and RBP domain-binding sequence, from 5' to 3'.

The RNA-guided nuclease-binding sequence of the gRNA and the catalytically-inactive RNA-guided nuclease (e.g., dCas9 protein) can form a complex that binds to a specific target polynucleotide sequence, based on the sequence complementarity between the DNA-targeting sequence and the target polynucleotide sequence. The DNA-targeting sequence of the gRNA provides target specificity to the complex via its sequence complementarity to the target polynucleotide sequence of a target DNA, as discussed below.

DNA-Targeting Sequence

The DNA-targeting sequence comprises a nucleotide sequence that is complementary to a specific sequence within the target DNA (e.g., breakpoint junction) (or the complementary strand of the target DNA). In other words, the DNA-targeting sequence interacts with a target polynucleotide sequence of the target DNA in a sequence-specific manner via hybridization (i.e., base pairing). As such, the nucleotide sequence of the DNA-targeting sequence may vary, and it determines the location within the target DNA that the gRNA and the target DNA will interact. The DNA-targeting sequence can be modified or designed (e.g., by genetic engineering) to hybridize to any desired sequence within the target DNA (e.g., breakpoint junction). In some embodiments, the DNA-targeting sequence is complementary to a sequence within a breakpoint junction, for example, the DNA-targeting sequence targets a unique sequence formed by ecDNA generation. In some embodiments, the target polynucleotide sequence is immediately 3' to a PAM (protospacer adjacent motif) sequence of the complementary strand, which can be 5'-CCN-3', wherein N is any DNA nucleotide. That is, in this embodiment, the complementary strand of the target polynucleotide sequence is immediately 5' to a PAM sequence that is 5'-NGG-3', wherein N is any DNA nucleotide. In related embodiments, the PAM sequence of the complementary strand matches the programmable nuclease (e.g., dCas9).

The DNA-targeting sequence can have a length of from about 12 nucleotides to about 100 nucleotides. For example, the DNA-targeting sequence can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the DNA-targeting sequence can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting sequence that is complementary to a target polynucleotide sequence of the target DNA (e.g., breakpoint junction) can have a length of at least about 12 nt. For example, the DNA-targeting sequence that is complementary to a target polynucleotide sequence of the target DNA can have a length at least about 12 nt, at least about 15 nt, at least about 18 nt, at least about 19 nt, at least about 20 nt, at least about 25 nt, at least about 30 nt, at least about 35 nt or at least about 40 nt. For example, the DNA-targeting sequence that is complementary to a target polynucleotide sequence of a target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt.

The nucleotide sequence of the DNA-targeting sequence that is complementary to the target polynucleotide sequence of the target DNA can have a length of at least about 12 nt. The percent complementarity between the DNA-targeting sequence and the target polynucleotide sequence of the target DNA (e.g., breakpoint junction) can be at least 50% (e.g., at least 55%, at least 60%, at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target polynucleotide sequence is 100% over the seven or eight contiguous 5'-most nucleotides of the target polynucleotide sequence.

In some cases, the percent complementarity between the DNA-targeting sequence and the target polynucleotide sequence is at least 60% over about 20 contiguous nucleotides. In some cases, the percent complementarity between the DNA-targeting sequence and the target polynucleotide sequence is 100% over the 7, 8, 9, 10, 11, 12, 13, or 14 contiguous 5'-most nucleotides of the target polynucleotide sequence (i.e., the 7, 8, 9, 10, 11, 12, 13, or 14 contiguous 3'-most nucleotides of the DNA-targeting sequence), and as low as 0% over the remainder. In such a case, the DNA-targeting sequence can be considered to be 7, 8, 9, 10, 11, 12, 13, or 14 nucleotides in length, respectively.

RNA-Guided Nuclease-Binding Sequence

The RNA-guided nuclease-binding sequence of the gRNA binds to the RNA-guided nuclease (e.g., catalytically-inactive RNA-guided nuclease). The RNA-guided nuclease and RNA-guided nuclease-binding sequence of the gRNA together bind to the target polynucleotide sequence recognized by the DNA-targeting sequence. The RNA-guided nuclease-binding sequence comprises two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the programmable nuclease-binding sequence, thus resulting in a stem-loop structure.

The RNA-guided nuclease-binding sequence can have a length of 10 nucleotides to 100 nucleotides, e.g., 10 nucleotides (nt) to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt. For example, the RNA-guided nuclease-binding sequence can have a length of 15 nucleotides (nt) to 80 nt, 15 nt to 50 nt, 15 nt to 40 nt, 15 nt to 30 nt, 37 nt to 47 nt (e.g., 42 nt), or 15 nt to 25 nt.

The dsRNA duplex of the RNA-guided nuclease-binding sequence can have a length 6 base pairs (bp) to 50 bp. For example, the dsRNA duplex of the programmable nuclease-binding sequence can have a length of 6 bp to 40 bp, 6 bp to 30 bp, 6 bp to 25 bp, 6 bp to 20 bp, 6 bp to 15 bp, 8 bp to 40 bp, 8 bp to 30 bp, 8 bp to 25 bp, 8 bp to 20 bp or 8 bp to 15 bp. For example, the dsRNA duplex of the RNA-guided nuclease-binding sequence can have a length of 8 bp to 10 bp, 10 bp to 15 bp, 15 bp to 18 bp, 18 bp to 20 bp, 20 bp to 25 bp, 25 bp to 30 bp, 30 bp to 35 bp, 35 bp to 40 bp, or 40 bp to 50 bp. In some embodiments, the dsRNA duplex of the RNA-guided nuclease-binding sequence has a length of 36 base pairs. The percent complementarity between the nucleotide sequences that hybridize to form the dsRNA duplex of the RNA-guided nuclease-binding sequence can be at least 60%. For example, the percent complementarity between the nucleotide sequences that hybridize to form the dsRNA duplex of the RNA-guided nuclease-binding sequence can be at least 65%, at least 70%, at least 75%, at least 80%, at least 85%, at least 90%, at least 95%, at least 98%, or at least 99%. In some cases, the percent complementarity between the nucleotide sequences that hybridize to form the dsRNA duplex of the RNA-guided nuclease-binding sequence is 100%.

The linker can have a length of 3 nucleotides to 100 nucleotides. For example, the linker can have a length of 3 nt to 90 nt, 3 nt to 80 nt, 3 nt to 70 nt, 3 nt to 60 nt, 3 nt to 50 nt, 3 nt to 40 nt, 3 nt to 30 nt, 3 nt to 20 nt, or 3 nt to 10 nt. For example, the linker can have a length of 3 nt to 5 nt, 5 nt to 10 nt, 10 nt to 15 nt, 15 nt to 20 nt, 20 nt to 25 nt, 25 nt to 30 nt, 30 nt to 35 nt, 35 nt to 40 nt, 40 nt to 50 nt, 50 nt to 60 nt, 60 nt to 70 nt, 70 nt to 80 nt, 80 nt to 90 nt, or 90 nt to 100 nt. In some embodiments, the linker is 4 nt.

Non-limiting examples of nucleotide sequences that can be included in a suitable RNA-guided nuclease-binding sequence (i.e., Cas9 handle) are set forth in SEQ ID NOs:

563-682 of WO 2013/176772 (see, for examples, FIGS. 8 and 9 of WO 2013/176772), incorporated herein by reference.

In some cases, a suitable RNA-guided nuclease-binding sequence comprises a nucleotide sequence that differs by 1, 2, 3, 4, or 5 nucleotides from any one of the above-listed sequences.

RNA-Binding Protein (RBP) Domain Binding Sequence(s)

The gRNA may comprise one or more tandem sequences, each of which can be specifically recognized and bound by a specific RNA-binding protein domain (e.g., a Pumilio-FBF (PUF) domain). Such sequences, referred to herein as RNA-binding protein (RBP) domain-binding sequences (e.g., PUF domain-binding sequences, PBS), may be engineered to bind any RBP binding domain (e.g., PUF domain). For example, based on the nucleotide-specific interaction between the individual PUF motifs of PUF domain and the single RNA nucleotide they recognize, the PBS sequences can be any designed sequences that bind their corresponding PUF domain.

In some embodiments, a PBS of the present disclosure has 8-mer. In some embodiments, a PBS of the present disclosure has 5, 6, 7, 8, 9, 10, 11, 12, 13, 14, 15, 16 or more RNA nucleotides.

In some embodiments, the PBS of the present disclosure has the sequence 5'-UGUAUAUA-3' and binds the wild-type human Pumilio 1 PUF domain. In some embodiments, the PBS of the present disclosure has the sequence 5'-UGUAUGUA-3', and binds the PUF domain PUF(3-2). In some embodiments, the PBS of the present disclosure has the sequence 5'-UUGAUAUA-3', and binds the PUF domain C. In some embodiments, the PBS of the present disclosure has the sequence 5'-UGGAUAUA-3', and binds the PUF domain PUF(6-2). In some embodiments, the PBS of the present disclosure has the sequence 5'-UUUAUAUA-3', and binds the PUF domain PUF(7-2). In some embodiments, the PBS of the present disclosure has the sequence 5'-UGUGU-GUG-3', and binds the PUF domain PUF[531]. In some embodiments, the PBS of the present disclosure has the sequence 5'-UGUAUAUG-3', and binds the PUF domain PUF(1-1). In some embodiments, the PBS of the present disclosure has the sequence 5'-UUUAUAUA-3' or 5'-UAUAUAUA-3', and binds the PUF domain PUF(7-1). In some embodiments, the PBS of the present disclosure has the sequence 5'-UGUAUUUA-3', and binds the PUF domain PUF(3-1). In some embodiments, the PBS of the present disclosure has the sequence 5'-UUUAUUUA-3', and binds the PUF domain PUF(7-2/3-1). Any one of the PUF domains described in WO 2016/148994 may be used as provided herein.

In some embodiments, one or more spacer region(s) separates two adjacent PBS sequences. The spacer regions may have a length of 3 nucleotides to 100 nucleotides. For example, the spacer can have a length of 3 nt to 90 nt, 3 nt to 80 nt, 3 nt to 70 nt, 3 nt to 60 nt, 3 nt to 50 nt, 3 nt to 40 nt, 3 nt to 30 nt, 3 nt to 20 nt or 3 nt to 10 nt. For example, the spacer can have a length of 3 nt to 5 nt, 5 nt to 10 nt, 10 nt to 15 nt, 15 nt to 20 nt, 20 nt to 25 nt, 25 nt to 30 nt, 30 nt to 35 nt, 35 nt to 40 nt, 40 nt to 50 nt, 50 nt to 60 nt, 60 nt to 70 nt, 70 nt to 80 nt, 80 nt to 90 nt, or 90 nt to 100 nt. In some embodiments, the spacer is 4 nt.

Detectable Conjugates

In order to detect the targeted breakpoint junction(s), at least one detectable molecule is required. In some embodiments, an RNA-binding protein (RBP) domain sequence (e.g., a PUF domain sequence) is linked to a detectable molecule (referred to herein as a detectable conjugate), which may be used for detecting the ecDNA in cells. In some embodiments, a breakpoint junction is genetically modified to express a detectable molecule, which can then be detected. Detection of ecDNA can be by any method known in the art including, but not limited to, imaging, binding assays, radiolabeling, Western blotting, and Southern blotting.

In some embodiments, detecting the ecDNA in cells is by imaging. Imaging, as used herein, refers to the visualization of detectable molecules bound to cellular structures (e.g., ecDNA).

The RBP domain, linked to the detectable molecule, hybridizes with the RBP domain binding sequence of the gRNA. The detectable molecule can then be imaged, indicating the target breakpoint junction locus or loci. The RBP domain sequence, in some embodiments, is a PUF domain.

PUF proteins (named after *Drosophila* Pumilio and *C. elegans* fern-3 binding factor) are known to be involve in mediating mRNA stability and translation. These proteins contain a unique RNA-binding domain known as the PUF domain. The RNA-binding PUF domain, such as that of the human Pumilio 1 protein (referred here also as PUM), contains 8 repeats (each repeat called a PUF motif or a PUF repeat) that bind consecutive bases in an anti-parallel fashion, with each repeat recognizing a single base—i.e., PUF repeats R1 to R8 recognize nucleotides N8 to N1, respectively. For example, PUM is composed of eight tandem repeats, each repeat consisting of 34 amino acids that folds into tightly packed domains composed of alpha helices. In some embodiments, the RBP domain-detectable molecule construct comprises 1, 2, 3, 4, 5, 6, 7, 8, 9, 10 or more PUF domains.

Each PUF repeat uses two conserved amino acids from the center of each repeat to specifically recognize the edge of one individual base within the RNA recognition sequence, and a third amino acid (Tyr, His or Arg) to stack between adjacent bases, causing a very specific binding between a PUF domain and an 8-mer RNA. For example, the code to recognize base U is the amino acid sequence "NYxxQ", whereas "(C/S)RxxQ" recognizes A and "SNxxE" recognizes G. These amino acids correspond to positions 12, 13, and 16 in the human Pumilio 1 PUF motif. The two recognition amino acid side chains at positions 12 and 16 in each PUF α-α-α repeat recognize the Watson-Crick edge of the corresponding base and largely determine the specificity of that repeat.

Therefore, the sequence specificity of the PUF domains can be altered precisely by changing the conserved amino acid (e.g., by site-directed mutagenesis) involved in base recognition within the RNA recognition sequence. By changing two amino acids in each repeat, a PUF domain can be modified to bind almost any 8-nt RNA sequence. This unique binding system makes PUF and its derivatives a programmable RNA-binding domain that can be engineered, in some embodiments, to bind a specific PUF domain binding sequence in the gRNA, and therefore, bringing the detection molecule to a specific PBS on the gRNA.

As used herein, "PUF domain" refers to a wildtype or naturally existing PUF domain, as well as a PUF homologue domain that is based on/derived from a natural or existing PUF domain, such as the prototype human Pumilio 1 PUF domain. The PUF domain of the present disclosure specifically binds to an RNA sequence (e.g., an 8-mer RNA sequence), wherein the overall binding specificity between the PUF domain and the RNA sequence is defined by sequence specific binding between each PUF motif/PUF repeat within the PUF domain and the corresponding single RNA nucleotide.

In some embodiments, the PUF domain comprises or consists essentially of 8 PUF motifs, each specifically recognizes and binds to one RNA nucleotide (e.g., A, U, G, or C).

In some embodiments, the PUF domain has more or less than 8 PUF motifs/repeats, e.g., the PUF domain comprises or consists essentially of 5, 6, 7, 8, 9, 10, 11, 12, 13, 14, 15, 16, or more PUF repeats/motifs, each specifically recognizes and binds to one RNA nucleotide (e.g., A, U, G, or C), so long as the PUF domain binds the RNA of 5, 6, 7, 8, 9, 10, 11, 12, 13, 14, 15, 16 or more nucleotides. By increasing or decreasing the number of PUF motifs, the length of the recognized RNA will be correspondingly increased or decreased. Since each PUF motif recognizes one RNA base, decreasing the domain by one motif decreases the length of the RNA recognized by one base; while increasing the domain by one motif increases the length of the RNA recognized by one base. Any number of motifs may be present. Therefore, in such embodiments, the specificity of the PUF domain-fusions of the present disclosure may be altered due to changes in PUF domain length. In some embodiments, the additional PUF motifs are inserted between two of the original PUF motifs, e.g., before the 1$^{st}$, between the 1$^{st}$ and the 2$^{nd}$, the 2$^{nd}$ and the 3$^{rd}$, the 3$^{rd}$, and the 4$^{th}$, the 4$^{th}$ and the 5$^{th}$, the 5$^{th}$ and the 6$^{th}$, the 6$^{th}$ and the 7$^{th}$, the 7$^{th}$ and the 8$^{th}$, or after the 8$^{th}$. In some embodiments, there are 1, 2, 3, 4, 5, 6, 7, 8, or more inserted PUF motifs between any of the insertion points above. For example, in some embodiments, there are 1, 2, 3, 4, 5, 6, 7, 8, or more inserted PUF motifs between the 5$^{th}$ and the 6$^{th}$ original PUF motif. Filipovska et al. (Nature Chemical Biology doi: 10.1038/NChemBio.577, published online: 15 May 2011) have reported an engineered PUF domain with 16 PUF motifs, including 8 additional PUF motifs inserted between the 5$^{th}$ and 6th original PUF motifs.

In some embodiments, the PUF domain comprises PUF motifs from different PUF domains from different proteins. For example, a PUF domain of the present disclosure may be constructed with PUF motifs from the human Pumilio 1 protein and one or more other PUF motifs from one or more other PUF proteins, such as PuDp or FBF. The RNA binding pockets of PUF domains have natural concave curvatures. Since different PUF proteins may have different curvatures, different PUF motifs in a PUF domain may be used to alter the curvature of the PUF domain. Altering the curvature is another method for altering the specificity and/or binding affinity of the PUF domain since flatter curvatures may allow for the recognition of more RNA bases.

Also included in the scope of the present disclosure are functional variants of the PUF domains or fusions thereof. The term "functional variant" as used herein refers to a PUF domain having substantial or significant sequence identity or similarity to a parent PUF domain, which functional variant retains the biological activity of the PUF domain of which it is a variant—e.g., one that retains the ability to recognize target RNA to a similar extent, the same extent, or to a higher extent in terms of binding affinity, and/or with substantially the same or identical binding specificity, as the parent PUF domain. The functional variant PUF domain can, for instance, be at least about 30%, 50%, 75%, 80%, 90%, 98% or more identical in amino acid sequence to the parent PUF domain. The functional variant can, for example, comprise the amino acid sequence of the parent PUF domain with at least one conservative amino acid substitution, for example, conservative amino acid substitutions in the scaffold of the PUF domain (i.e., amino acids that do not interact with the RNA). Alternatively or additionally, the functional variants can comprise the amino acid sequence of the parent PUF domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent PUF domain, or may alter the stability of the PUF domain to a desired level (e.g., due to substitution of amino acids in the scaffold). The PUF domain can consist essentially of the specified amino acid sequence or sequences described herein, such that other components, e.g., other amino acids, do not materially change the biological activity of the functional variant.

In some embodiments, the PUF domain is a Pumilio homology domain (PU-HUD). In a particular embodiment, the PU-HUD is a human Pumilio 1 domain. The sequence of the human PUM is known in the art and is reproduced below:

```
                                    (SEQ ID NO: 1)
GRSRLLEDFRNNRYPNLQLREIAGHIMEFSQDQHGSRFIQLKLERATPAE

RQLVFNEILQAAYQLMVDVFGNYVIQKFFEFGSLEQKLALAERIRGHVLS

LALQMYGCRVIQKALEFIPSDQQNEMVRELDGHVLKCVKDQNGNHVVQKC

IECVQPQSLQFIIDAFKGQVFALSTHPYGCRVIQRILEHCLPDQTLPILE

ELHQHTEQLVQDQYGNYVIQHVLEHGRPEDKSKIVAEIRGNVLVLSQHKF

ASNVVEKCVTHASRTERAVLIDEVCTMNDGPHSALYTMMKDQYANYVVQK

MIDVAEPGQRKIVMHKIRPHIATLRKYTYGKHILAKLEKYYMKNGVDLG
```

The wild-type human PUM specifically binds the Nanos Response Element (NRE) RNA, bearing a core 8-nt sequence 5'-UGUAUAUA-3'.

In some embodiments, the PUF domain of the present disclosure is any PUF protein family member with a Pum-HD domain. Non-limiting examples of a PUF family member include FBF in *C. elegans*, Ds pum in *Drosophila*, and PUF proteins in plants such as *Arabidopsis* and rice. A phylogenetic tree of the PUM-HDs of *Arabidopsis*, rice and other plant and non-plant species is provided in Tam et al. ("The Puf family of RNA-binding proteins in plants: phylogeny, structural modeling, activity and subcellular localization." BMC Plant Biol. 10:44, 2010, the entire contents of which are incorporated by reference herein).

Figure 5:
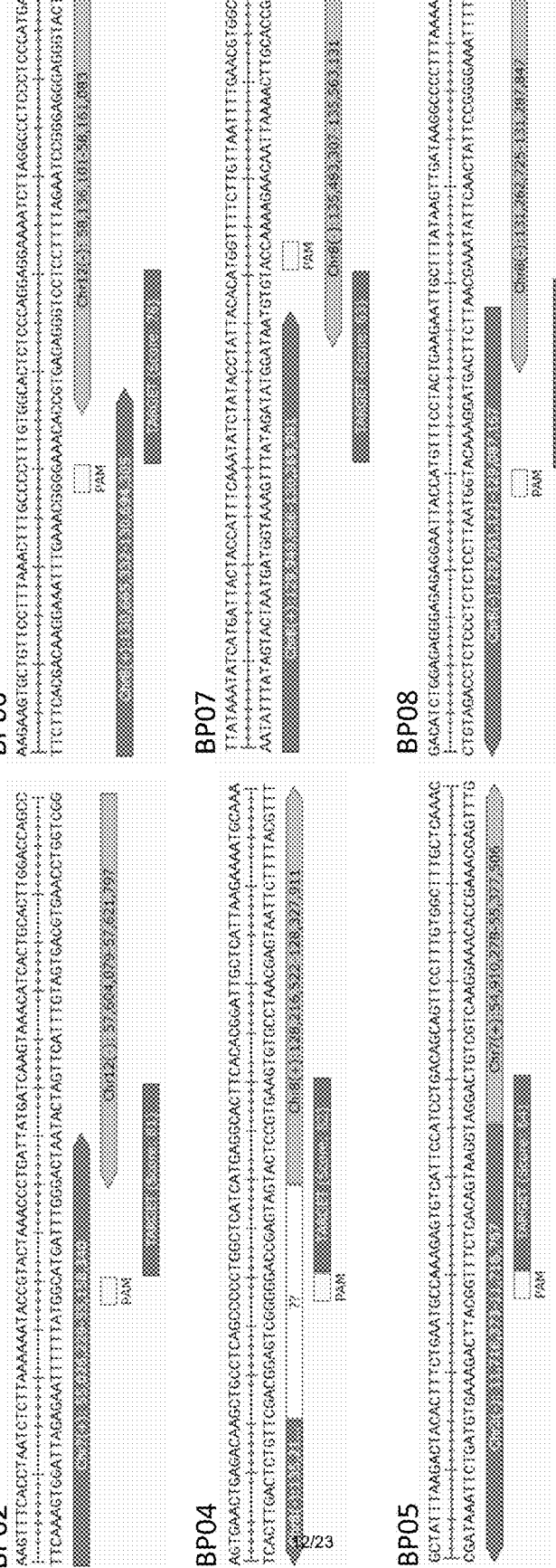
FIG. 5. Target breakpoint junctions and guide RNA design. Each breakpoint junction was selected according to the presence of available PAM sequence. The unique specificity of each breakpoint was scored by CRISPOR (crispor.tefor.net). Sequences from top to bottom, left to right, correspond to SEQ ID NOs: 14-25.

PUF family members are highly conserved from yeast to human, and all members of the family bind to RNA in a sequence specific manner with a predictable code. The accession number for the domain is PS50302 in the Prosite database (Swiss Institute of Bioinformatics) and a sequence alignment of some of the members of this family is shown in FIGS. 5 & 6 of WO 2011-160052 A2 (ClustalW multiple sequence alignment of human, mouse, rat Pumilio 1 (hpum1, Mpum1, Ratpum1) and human and mouse Pumilio 2 (hpum2, Mpum2), respectively.

Any of the PUF domain can be made using, for example, a Golden Gate Assembly kit (see Abil et al., Journal of Biological Engineering 8:7, 2014), which is available at Addgene (Kit #1000000051).

Catalytically-Inactive RNA-Guided Nuclease

In some embodiments, the catalytically-inactive RNA-guided nuclease is a modified Cas9 protein, such as dead Cas9 (dCas9) protein. In some embodiments, the dCas9 has substantially no detectable endonuclease (e.g., endodeoxy-ribonuclease) activity. In some embodiments when a dCas9 has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the polypeptide can still bind to target DNA in a site-specific manner, because it is still guided to a target polynucleotide sequence by a DNA-targeting sequence of gRNA, as long as it retains the ability to interact with the Cas9-binding sequence of the gRNA.

In some cases, the dCas9 has a reduced ability to cleave both the complementary and the non-complementary strands of the target DNA. As a non-limiting example, in some cases, the dCas9 harbors both D10A and H840A mutations of the amino acid sequence depicted in FIG. 3 of WO 2013/176772 or the corresponding mutations of any of the amino acid sequences set forth in SEQ ID NOs: 1-256 and 795-1346 of WO 2013/176772 (all such sequences incorporated by reference).

Other Programmable Nuclease Systems for Detecting ecDNA

The cells, methods, and compositions provided herein further enable, in some embodiments, detecting ecDNA that is genetically modified at a breakpoint junction. The breakpoint junction may be genetically modified to express a detectable molecule. Genetic modification of the breakpoint junction may be by any method known in the art including programmable nucleases and gene knockout. In some embodiments, the breakpoint junction is genetically modified using a programmable nuclease.

Genetically-modified breakpoint junctions may be detected if the breakpoint junction has been modified to express a detectable molecule. In some embodiments, the detectable molecule is a fluorescent protein that is detected by imaging.

In some aspects, the present disclosure provides methods of genetically modifying breakpoint junctions in ecDNA in cells. Genetically modifying means altering a breakpoint junction nucleotide sequence. Genetic modifications may include insertions, deletions, and mutations of the breakpoint junction nucleotide sequence. Insertions into breakpoint junction sequences may comprise coding regions that produce proteins (e.g., detectable molecules) or non-coding regions that regulate gene expression (e.g., activate gene expression or repress gene expression). Deletions from breakpoint junction sequences may comprise deleting a sequence comprising a breakpoint junction or a portion of the breakpoint junction. Mutations in breakpoint junctions may be a portion (e.g., at least one nucleotide, at least 2 nucleotides, at least 3 nucleotides, at least 4 nucleotides, at least 5 nucleotides) of the breakpoint junction or all of the breakpoint junction.

Breakpoint junctions in ecDNA in cells may be modified by any method known in the art. Non-limiting methods of modifying breakpoint junctions include utilizing programmable nuclease and gene knockout using Floxed alleles. In some embodiments, genetic modification of breakpoint junction uses a programmable nuclease-based gene editing system. A programmable nuclease is an enzyme that specifically binds and cuts a target sequence (e.g., breakpoint junction). In some embodiments, programmable nucleases are guided to a target sequence by a gRNA that is complementary to the target sequence (e.g., breakpoint junction). Such nucleases are known as RNA-guided nucleases (e.g., Cas9, dCas9, Cpf1). In some embodiments, programmable nucleases are guided to a target sequence by protein DNA binding domains (e.g., zinc finger domains, transcription activator-like effector domains).

A programmable nuclease gene-based gene-editing system may include a programmable nuclease, a guide RNA that is complementary to the target sequence (e.g., breakpoint junction), and a donor nucleic acid for modifying the target sequence. A gRNA for use in genetically-modifying a breakpoint junction may comprise a DNA targeting sequence and a nuclease binding sequence as described previously.

A donor nucleic acid may include a nucleotide sequence to be inserted after the breakpoint junction has been cut by the programmable nuclease. If the nucleotide sequence was not previously present in the breakpoint junction and is introduced, an insertion has occurred. If a nucleotide sequence was present in the breakpoint junction and is removed upon repair of the donor nucleic acid, a deletion has occurred. If a nucleotide sequence that was present in the breakpoint junction is altered upon repair with the donor nucleic acid, a mutation has occurred.

The nucleotide sequence to be inserted into a breakpoint junction may be a coding sequence. A coding sequence, when expressed, produces a protein (e.g., detectable molecule). In some embodiments, the nucleotide sequence to be inserted is not a coding sequence (e.g., promoter, enhancer, repressor).

Programmable nucleases cut at or near target sequences (e.g., breakpoint junctions), forming DNA double-stranded breaks (DSBs). Cutting at a target sequence means cutting within the nucleotide sequence that is recognized by the programmable nuclease. Cutting near a target sequence may be within 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides.

DNA DSBs made by programmable nucleases are repaired by error-free homologous recombination (HR) or error-prone non-homologous end-joining (NHEJ). A donor nucleic acid with homology arms to that are complementary to the sequences of the breakpoint junction will promote repair of the DSB by HR and inclusion of the nucleotide sequence between the homology arms. Homology arms are single-stranded nucleotide sequences that are complementary to the nucleotide sequences at a DNA DSB. After a DNA DSB is made, one strand of the DSB on each side of the break is resected, forming single-stranded DNA. This single stranded DNA binds to the complementary homology arms in the donor nucleic acid, which will be incorporated into the breakpoint junction upon repair. Homology arms need not be the same size and may be at least 5 nucleotides, at least 10 nucleotides, at least 15 nucleotides, at least 20 nucleotides, at least 25 nucleotides, at least 30 nucleotides, at least 35 nucleotides, or at least 40 nucleotides.

If a donor nucleic is not provided with a programmable nuclease, the DSB at or near the breakpoint junction may be repaired by either HR or NHEJ. NHEJ is an error-prone process, in which DNA breaks are joined without regard to complementary sequences. Thus, repair of DSB by NHEJ may produce a deletion in a breakpoint junction if sequence is removed upon repair, or a mutation if the nucleotide sequence is altered upon repair.

Catalytically-Active RNA-Guided Nucleases

Breakpoint junctions in ecDNA may be genetically modified by catalytically-active RNA-guided programming nucleases. In some embodiments, the catalytically-active RNA-guided nuclease is a Clustered Regularly Interspace Palindromic Repeats-Associated (CRISPR/Cas) nuclease. CRISPR/Cas nucleases exist in a variety of bacterial species, where they recognize and cut specific DNA sequences. The CRISPR/Cas nuclease are grouped into two classes. Class 1 systems use a complex of multiple CRISPR/Cas proteins to bind and degrade nucleic acids, whereas Class 2 systems use a large, single protein for the same purpose. A CRISPR/Cas nuclease as used herein may be selected from Cas9, Cas10, Cas3, Cas4, C2c1, C2c3, Cas13a, Cas13b, Cas13c, and Cas14 (e.g., Harrington, L. B. et al., *Science,* 2018 (DOI: 10.1126/scienceaav4294)).

CRISPR/Cas nuclease from different bacterial species have different properties (e.g., specificity, activity, binding affinity). In some embodiments, orthogonal catalytically-active RNA-guided nuclease species are used. Orthogonal species are distinct species (e.g., two or more bacterial species). For example, a first catalytically-active Cas9 nuclease as used herein may be a *Neisseria meningitidis* Cas9 and a second catalytically-active Cas9 nuclease as used herein may be a *Streptococcus thermophilus* Cas9.

Non-limiting examples of bacterial CRISPR/Cas9 nucleases for use herein include *Streptococcus thermophilus* Cas9, *Streptococcus thermophilus* Cas10, *Streptococcus thermophilus* Cas3, *Staphylococcus aureus* Cas9, *Staphylococcus aureus* Cas10, *Staphylococcus aureus* Cas3, *Neisseria meningitidis* Cas9, *Neisseria meningitidis* Cas10, *Neisseria meningitidis* Cas3, *Streptococcus pyogenes* Cas9, *Streptococcus pyogenes* Cas10, and *Streptococcus pyogenes* Cas3.

In some embodiments, a catalytically-active RNA-guided nuclease is a RNA-guided FokI nuclease (RFN). FokI nucleases are bacterial endonucleases with an N-terminal DNA-binding domain and a C-terminal endonuclease domain. The DNA-binding domain binds to a 5'-GGATG-3' target sequence, after which the endonuclease domain cleaves in a non-sequence specific manner. RFN is a fusion protein derived from *Streptococcus pyogenes* dCas9 fused to the FokI nuclease domain. A fusion protein is a protein that includes at least two domains that are encoded by separate genes that have been joined so that they are transcribed and translated as a single unit, producing a single polypeptide. In some embodiments, a catalytically-inactive RNA-guided nuclease is a RFN, which has a greater DNA-binding specificity than FokI nuclease due to the *Streptococcus pyogenes* dCas9.

In some embodiments, a catalytically-active RNA-guided nuclease is a CRISPR-associated endonuclease in *Prevotella* and *Francisella* 1 (Cpf1). Cpf1 is a bacterial endonuclease similar to Cas9 nuclease in terms of activity. However, Cpf1 only requires a short (~42 nucleotide) gRNA, while Cas9 requires a longer (~100 nucleotide) gRNA. Additionally, Cpf1 cuts the DNA 5' to the target sequence and leaves blunted ends, while Cas9 leaves sticky ends with DNA overhangs. Cpf1 proteins from Acidaminococcus and Lachnospiraceae bacteria efficiently cut DNA in human cells in vitro. In some embodiments, the RNA-guided nuclease is Acidaminococcus Cpf1 or Lachnospiraceae Cpf1, which require shorter gRNAs than Cas nuclease proteins.

Zinc-Finger Nucleases

Methods described herein, in some embodiments, include the use of zinc-finger nucleases to genetically modify breakpoint junctions in ecDNA. A zinc-finger nuclease (ZFN) is an endonuclease that can be programmed to cut specific sequences of DNA. ZFNs are composed of a zinc-finger DNA-binding domain and a nuclease domain.

The DNA-binding domains of individual ZFNs generally contain 3-6 individual zinc finger repeats that recognize 9-18 nucleotides. For example, if the zinc finger domain perfectly recognizes a 3 base pair sequence, then a 3 zinc finger array can be generated to recognize a 9 base pair target DNA sequence. Because individual zinc fingers recognize relatively short (e.g., 3 base pairs) target DNA sequences, ZFNs with 4, 5, or 6 zinc finger domains are typically used to minimize off-target DNA cutting. Non-limiting examples of zinc finger DNA-binding domains that may be used with methods of the present disclosure include Zif268, Ga14, HIV nucleocapsid protein, MYST family histone acetyltransferases, myelin transcription factor Myt1, and suppressor of tumurigenicity protein 18 (ST18). A ZFN may contain homogeneous DNA binding domains (all from the same source molecule) or a ZFN may contain heterogeneous DNA binding domains (at least one DNA binding domain is from a different source molecule).

Zinc finger DNA-binding domains work in concert with a nuclease domain to form a zinc finger nucleases (ZFNs) that cut target DNA (e.g., breakpoint junction). The nuclease cuts the DNA in a non-sequence specific manner after being recruited to the target DNA (e.g., breakpoint junction) by the zinc fingers DNA-binding domains. The most widely-used ZFN is the type II restriction enzyme FokI, which forms a heterodimer before producing a double-stranded break in the DNA. Thus, two ZFN proteins must bind to opposite strands of DNA to create the FokI heterodimer and form a double-stranded break, reducing off-target DNA cleavage events (Kim, et al., Proc Natl Acad Sci USA, 1996, 93(3): 1156-1160). Additionally, ZFNs may be nickases that only cleave one strand of the double-stranded DNA. By cleaving only one strand, the DNA is more likely to be repaired by error-free HR as opposed to error-prone NHEJ (Ramirez, et al., *Nucleic Acids Research,* 40(7): 5560-5568). Non-limiting examples of nucleases that may be used with methods in this disclosure include FokI and DNaseI.

In some embodiments, a breakpoint junction in ecDNA in a cell is genetically modified using a ZFN-based gene editing system. The ZFN-gene based gene editing system may comprise (i) a ZFN, or a nucleic acid encoding a ZFN, that binds to the breakpoint junction, and (ii) a donor nucleic acid comprising a coding region that encodes a detectable molecule (e.g., fluorescent protein), wherein the coding region is flanked by homology arms that are complementary to sequences of the breakpoint junction.

In some embodiments, the ZFN-based gene editing system introduces insertions (e.g., detectable molecules) into the breakpoint junction in ecDNA. In some embodiments, the ZFN-based gene editing system introduces deletions from the breakpoint junction in ecDNA (e.g., cancer-promoting genes). In some embodiments, the ZFN-based gene editing system introduces mutations into the breakpoint junction in ecDNA (e.g., activate gene expression, suppress gene expression).

It should be understood that the ZFN in the ZFN-based gene editing system may be expressed as a fusion protein, with the DNA-binding domain and the nuclease domain expressed in the same polypeptide. This fusion may include a linker of amino acids (e.g., 1, 2, 3, 4, 5, 6, or more) between the DNA-binding domain and the nuclease domain.

Transcription Activator-Like Effector Nucleases

Methods described herein, in some embodiments, include the use of transcription activator-like effector nucleases (TALENs) to genetically-modify breakpoint junctions in ecDNA. A TALEN is a endonuclease that can be programmed to cut specific sequences of DNA. TALENs are composed of transcription activator-like effector (TALE) DNA-binding domains, which recognize single target nucleotides in the DNA, and transcription activator-like effector nucleases (TALENs) which cut the DNA at or near the target nucleotide.

Transcription activator-like effectors (TALEs) found in bacteria are modular DNA binding domains that include central repeat domains made up of repetitive sequences of residues (Boch J. et al. *Annual Review of Phytopathology* 2010; 48: 419-36; Boch J Biotechnology 2011; 29(2): 135-136). The central repeat domains, in some embodiments, contain between 1.5 and 33.5 repeat regions, and each repeat region may be made of 34 amino acids; amino acids 12 and 13 of the repeat region, in some embodiments, determines the nucleotide specificity of the TALE and are known as the repeat variable diresidue (RVD) (Moscou M J et al. *Science* 2009; 326 (5959): 1501; Juillerat A et al. Scientific Reports 2015; 5: 8150). Unlike ZF DNA sensors, TALE-based sequence detectors can recognize single nucleotides. In some embodiments, combining multiple repeat regions produces sequence-specific synthetic TALEs (Cermak T et al. *Nucleic Acids Research* 2011; 39 (12): e82). Non-limiting examples of TALEs that may be utilized in the present disclosure include IL2RG, AvrBs, dHax3, and thXoI.

A transcription activator-like effector nuclease (TALEN) cleaves the DNA non-specifically after being recruited to the target sequence by the TALE. This non-specific cleavage can lead to off-target DNA cleavage events. The most widely-used TALEN is the type II restriction enzyme FokI, which forms a heterodimer to produce a double-stranded break in DNA. Thus, two TALEN proteins must bind to opposite strands of DNA to create the FokI heterodimer and form a double-stranded break, reducing off-target DNA cleavage events (Christian M et al. Genetics 2010; 186: 757-761). Additionally, TALEN nucleases may be nickases, which cut only a single-strand of the DNA, thus promoting repair of the break by HR (Gabsalilow L. et al. *Nucleic Acids Res.* 41, e83). Non-limiting examples of TALENs that may be utilized in the present disclosure include FokI, RNAseH, and MutH.

In some embodiments, a breakpoint junction in ecDNA in a cell is genetically modified using a TALEN-based gene editing system. The TALEN-gene based gene editing system may comprise (i) a TALEN, or a nucleic acid encoding a TALEN, that binds to the breakpoint junction, and (ii) a donor nucleic acid comprising a coding region that encodes a detectable molecule (e.g., fluorescent protein), wherein the coding region is flanked by homology arms that are complementary to sequences of the breakpoint junction.

In some embodiments, the TALEN-based gene editing system introduces insertions (e.g., detectable molecules) into the breakpoint junction in ecDNA. In some embodiments, the TALEN-based gene editing system introduces deletions from the breakpoint junction in ecDNA (e.g., cancer-promoting genes). In some embodiments, the TALEN-based gene editing system introduces mutations into the breakpoint junction in ecDNA (e.g., activate gene expression, suppress gene expression).

It should be understood that the TALEN in the TALEN-based gene editing system may be expressed as a fusion protein, with the DNA-binding domain and the nuclease domain expressed in the same polypeptide. This fusion may include a linker of amino acids (e.g., 1, 2, 3, 4, 5, 6, or more) between the DNA-binding domain and the nuclease domain.

Cells

As discussed above, the methods described herein may be used to detect breakpoint junctions in ecDNA in live cells (e.g., in vivo, in vitro, and/or in situ). Because the gRNA provides specificity by hybridizing to target polynucleotide sequence of a target DNA, the cells include, but are not limited to, a bacterial cell; an archaeal cell; a single-celled eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium falciparum*; a helminth; etc.); a cell from a vertebrate animal (e.g., fish, amphibian, reptile, bird, mammal); a mammalian cell, e.g., a rodent cell, a human cell, a non-human primate cell, etc. Suitable cells for imaging include naturally-occurring cells; genetically modified cells (e.g., cells genetically modified in a laboratory, e.g., by the "hand of man"); and cells manipulated in vitro in any way. In some embodiments, a cell is isolated or cultured.

Any type of cell may be of interest (e.g., a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells," "primary cell lines," and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. In some embodiments, the cells are grown in culture. If the cells are primary cells, such cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or other solutions commonly used in the art to preserve cells at such freezing temperatures, and thawed in a manner as commonly known in the art for thawing frozen cultured cells.

In some embodiments, cells of the present disclosure are cancer cells. The cancer cells may be primary cancer cells or recurrent cancer cells. A primary cancer cell is a cell isolated during the first instance of cancer in a subject (e.g., a human subject). A recurrent cancer cells is a cell isolated during a subsequent (e.g., second, third, fourth, fifth, sixth, seventh, eighth, ninth, or tenth) instance of cancer in a subject. Non-limiting embodiments of such cancer cells that can be used in the present disclosure are glioblastoma cells, breast cancer cells, colon cancer cells, lung cancer cells, melanoma cells, sarcoma cells, esophageal cancer cells, renal cancer cells, ovarian cancer cells, hematopoietic cancer cells, prostate cancer cells, pancreatic cancer cells, medullablastoma cancer cells, bone cancer cells, uterine cancer cells, cervical cancer cells, vaginal cancer cells, prostate cancer cells.

Introduction of gRNA, Programmable Nuclease, and Detectable Molecule Construct into Cells The gRNA, programmable nuclease (e.g., dCas9, Cas9, ZFN, TALEN), and/or detectable molecule (or other component of a system provided herein) can be introduced into a cell by any cell transfection methods, including but not limited to viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., *Adv. Drug Deliv. Rev., pii:* 50169-409X(12)00283-9.doi:10.1016/j.addr.2012.09.023), and the like. In some embodiments, the gRNA, programmable nuclease (e.g., dCas9, Cas9, ZFN, TALEN), and/or detectable molecule (or other component of a system provided herein) are introduced into the cell via transfection.

ecDNA in cells may be detected through imaging using, for example, a fluorescent protein. Imaging may occur 12-96 hours after transfection. For example, imaging may occur 12, 24, 36, 48, 60, 72, 84, or 96 hours after transfection. As another example, imaging may occur 12-24, 12-48, 12-72, 24-48, 24-72, or 48-72 hours post-transfection. Imaging may occur for less than 1, 2, 3, 4, 5, 6, 7, 8, 9, 10, 11, 12, 13, 14, or 15 minutes. In some embodiments, images are taken at certain time points, for example, every 1, 2, 3, 4, 5, 6, 7, 8, 9, 10, 15, 20, 25, 30, 35, 40, 45, 50, 55, or 60 minutes. In some embodiments, imaging takes place over a period of 1, 2, 3, 4, 5, 6, 7, 8, 9, 10, 11, 12, 14, 16, 18, 20, 24, 36, 48, 60, or 72 hours. For example, images may be captured every 30 minutes for 5, 6, 7, 8, 9, 10, 11, 12, 13, 14, 15, 16, 17, 18, 19, or 20 hours.

Thus, the present disclosure also provides an isolated nucleic acid comprising a nucleotide sequence encoding the gRNA. In some cases, the isolated nucleic acid also comprises a nucleotide sequence encoding a programmable nuclease (e.g., dCas9, Cas9, ZFN, TALEN). In some embodiments, the ZFN and TALEN programmable nucleases may be expressed as fusion proteins and encoded on the same nucleic acid molecule. In some embodiments, the DNA-binding domains and nuclease domains of ZFNs and TALENs would be expressed on separate nucleic acids. In some embodiments, the present disclosure also provides an isolated nucleic acid encoding the donor nucleic acid.

In some embodiments, the programmable nuclease (e.g., dCas9, Cas9, ZFN, TALEN), the gRNA containing PUF binding sites, and PUF-detectable molecule construct are cloned into separate plasmids. The plasmids may then be linearized using any method known in the art (e.g., with BgIII), and then subjected to in vitro transcription. The resulting linear plasmid DNA is then used to transfect the cells. In some embodiments, more than one gRNA is used (e.g., to detect multiple loci). In these instances, each gRNA may be added in equal amounts (e.g., 33 ng of each gRNA plasmid), or in unequal amounts (e.g., 33 ng of one gRNA plasmid, and 67 ng of a different gRNA plasmid).

In some embodiments, a method involves introducing into a cell (or a population of cells) one or more nucleic acids (e.g., vectors) comprising nucleotide sequences encoding a single gRNA and/or a programmable nuclease (e.g., dCas9 protein, Cas9, ZFN, TALEN) and/or a detectable molecule construct (e.g., a PUF domain linked to a fluorescent protein, donor nucleic acid containing coding region that encodes detectable molecule). In some embodiments, the cell comprising a target DNA is in vitro. Suitable nucleic acids comprising nucleotide sequences encoding a single gRNA and/or a programmable nuclease (e.g., dCas9, Cas9, ZFN, TALEN protein) and/or a detectable molecule construct (e.g., a PUF domain linked to a fluorescent protein, donor nucleic acid containing coding region that encodes detectable molecule) include expression vectors, where the expression vectors may be recombinant expression vector.

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., *Invest Opthalmol. Vis. Sci.*, 35:2543-2549, 1994; Borras et al., *Gene Ther.*, 6:515-524, 1999; Li and Davidson, *Proc. Natl. Acad. Sci. USA*, 92:7700-7704, 1995; Sakamoto et al., *Hum. Gene Ther.*, 5:1088-1097, 1999; WO 94/12649, WO 93/03769; WO 93/19191; WO 94/28938; WO 95/11984 and WO 95/00655); adeno-associated virus (see, e.g., Ali et al., *Hum. Gene Ther.*, 9:81-86, 1998, Flannery et al., *Proc. Natl. Acad. Sci. USA*, 94:6916-6921, 1997; Bennett et al., *Invest Opthalmol Vis Sci* 38:2857-2863, 1997; Jomary et al., *Gene Ther.*, 4:683-690, 1997, Rolling et al., *Hum. Gene Ther.*, 10:641-648, 1999; Ali et al., *Hum. Mol. Genet.*, 5:591-594, 1996; Srivastava in WO 93/09239, Samulski et al., *J. Vir.*, 63:3822-3828, 1989; Mendelson et al., *Virol.*, 166: 154-165, 1988; and Flotte et al., *Proc. Natl. Acad. Sci. USA*, 90: 10613-10617, 1993); SV40; herpes simplex virus; human immunodeficiency virus (see, e.g., Miyoshi et al., *Proc. Natl. Acad. Sci. USA*, 94: 10319-23, 1997; Takahashi et al., *J. Virol.*, 73:7812-7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, HIV virus, myeloproliferative sarcoma virus, and mammary tumor virus); and the like.

Numerous suitable expression vectors are known to those skilled in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al., *Methods in Enzymology*, 153:516-544, 1987).

Kits

The present disclosure also provides a kit for carrying out a method. A kit may comprise: (a) a single gRNA of the present disclosure, or a nucleic acid (e.g., vector) comprising a nucleotide sequence encoding the same; optionally, (b) a programmable RNA nuclease (e.g., dCas9, Cas9, ZFN, TALEN protein), or a vector encoding the same (including an expressible mRNA encoding the same); and optionally, (c) one or more RBP domains (e.g., PUF domains) linked to detectable molecules, or a vector encoding the same (including an expressible mRNA encoding the same); and, further optionally, (d) a donor nucleic acid comprising a coding region that encodes a detectable molecule (e.g., fluorescent protein), or a vector encoding the same (including an expressible mRNA encoding the same).

In some embodiments, one or more of (a)-(d) may be encoded by the same vector.

In some embodiments, the kit also comprises one or more buffers or reagents that facilitate the introduction of any one of (a)-(d) into a host cell, such as reagents for transformation, transfection, or infection.

For example, a kit can further include one or more additional reagents, where such additional reagents can be selected from: a buffer; a wash buffer; a control reagent; a control expression vector or RNA polynucleotide; a reagent for in vitro production of the programmable nuclease (e.g., dCas9, Cas9, ZFN, TALEN) or RBP domain construct from DNA; and the like.

Components of a kit can be in separate containers; or can be combined in a single container.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Compositions

The present disclosure also provides compositions. The compositions may include any of the cells, nucleic acids, gRNAs, programmable nucleases, or other structures as described herein. In some embodiments, a composition comprises cells, nucleic acids, gRNAs, and programmable nucleases. In some embodiments, a composition comprises cells, nucleic acids, gRNAs, or programmable nucleases.

A composition comprising cells may comprise multiple cell types. In some embodiments, a composition comprising cells comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 cell types.

A composition comprising nucleic acids may comprise nucleic acids encoding multiple proteins. In some embodiments, a composition comprising nucleic acids comprises nucleic acids encoding at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 proteins.

A composition comprising gRNAs may comprise gRNAs that are complementary to multiple target sequences (e.g., breakpoint junctions). In some embodiments, a composition comprising gRNAs comprises gRNAs that are complementary to at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 target sequences.

A composition comprising programmable nucleases may comprise programmable nucleases that target multiple sequences (e.g., breakpoint junctions). In some embodiments, a composition comprising programmable nucleases comprises programmable nucleases that target at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 target sequences.

In some embodiments, any of the compositions described herein further comprise at least one carrier. A carrier is a compound that preserves the function of the molecules in the composition.

Non-limiting examples of carriers that may be used with compositions described herein include liposomes, microspheres, nanocarriers, sodium chloride, potassium chloride, magnesium chloride, sodium phosphate, sodium citrate, potassium citrate, HEPES, EDTA, magnesium, zinc, sodium, manganese, Penicillin, streptomycin, gentamycin, hygromycin, fetal bovine serum, and bovine serum albumin.

EXAMPLES

Figure 1E:
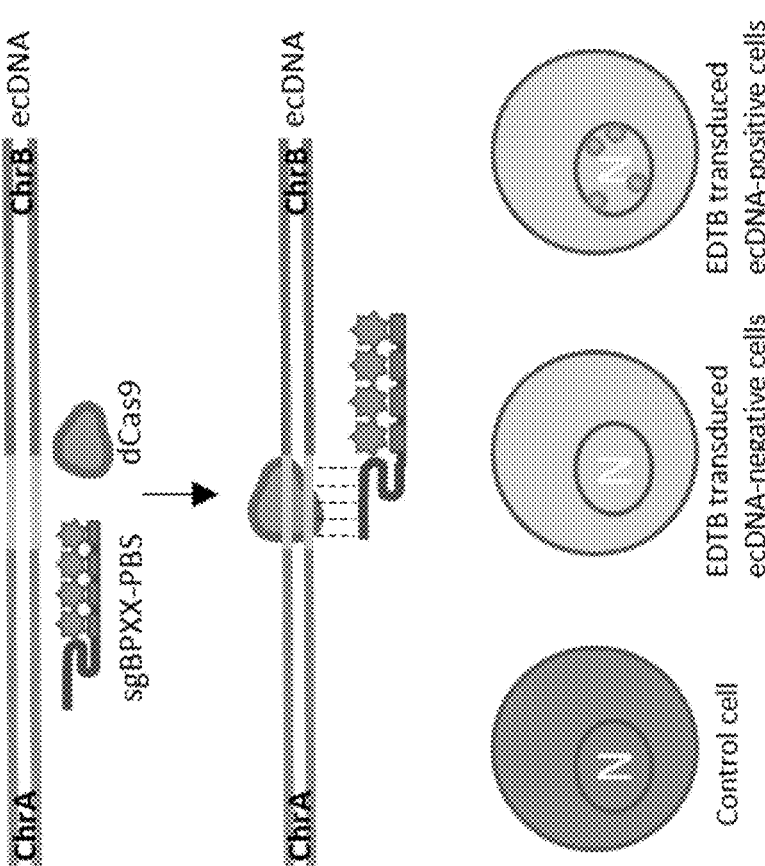

During extrachromosomal DNA (ecDNA) generation, the rearrangement of various chromosomal fragments generates junctions unique to the structure (FIG. 1A). The sequence of nucleotides spanning a junction is the breakpoint junction (FIG. 1A, black arrow). These breakpoint junctions have not been found in any autosomal sequences; thus, these breakpoint junctions were selected as targets to implement EDTv2. EDTv2 employs the Casilio system, which uses catalytically deactivated Cas9 (dCas9) to secure the GFP sequence at the specific breakpoint region of ecDNA (FIG. 1D). This includes a breakpoint-specific gRNA that includes a PUF binding site (PBS) (sgBPXX), dCas9, and PUF-fused GFP (enabling formation of a tripartite complex of the gRNA, dCas9, and GFP). dCas9 may be expressed on a plasmid and introduced with sgBPXX and PUF-fused GFP into cells (e.g. primary and recurrent cell lines). Once the cells are transduced with the EDTBv2, cells express PUF-fused GFP (FIG. 1E).

Example 1: Identification and Validation of Breakpoint Junctions

Figure 2:
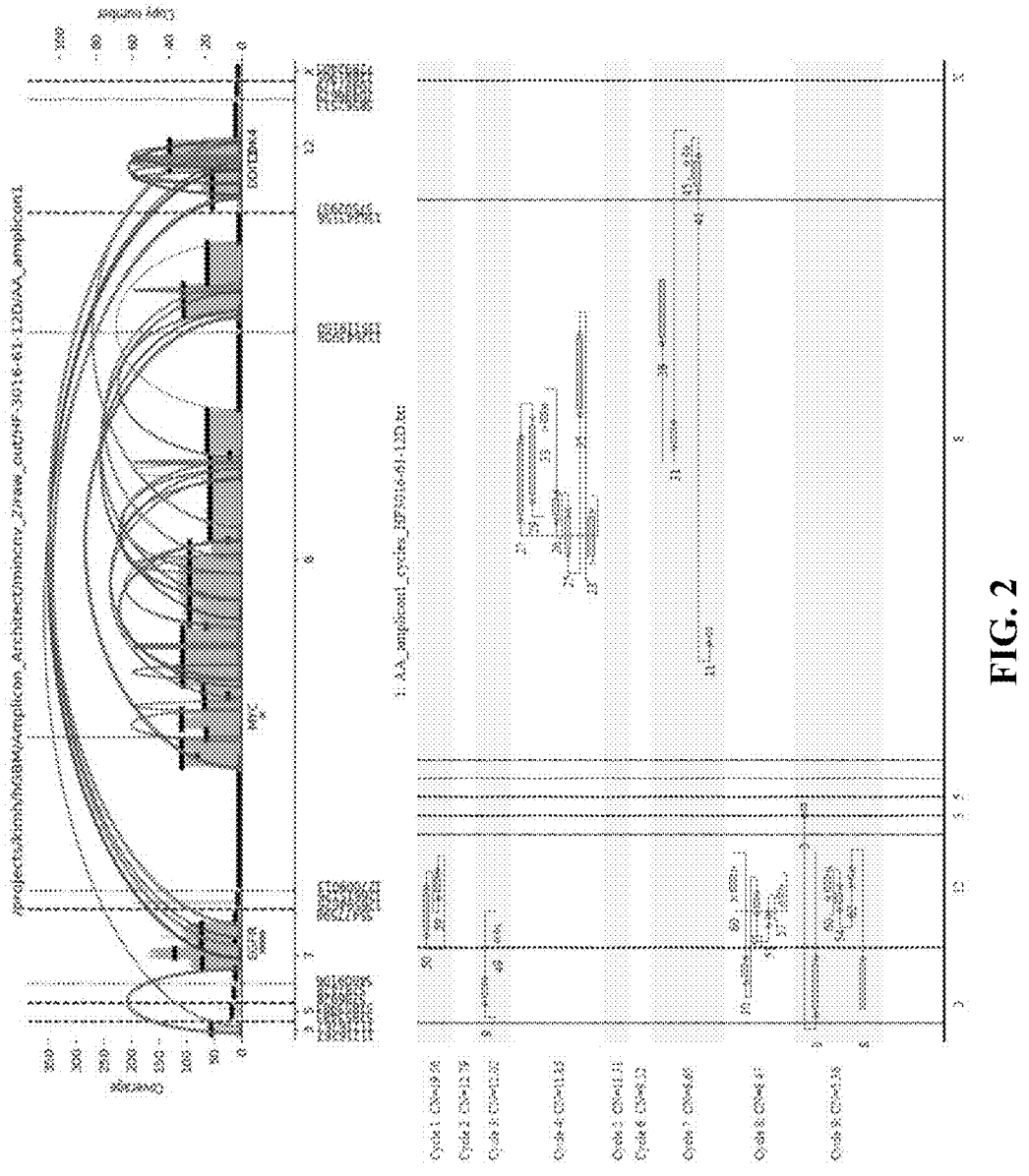
FIG. 2. Inferring precise ecDNA breakpoint junctions from whole genome sequencing data (top panel). Predicting ecDNA structures from the HF3016 glioblastoma neurosphere cell line model, using AmpliconArchitech (github-.com/virajbdeshpande/AmpliconArchitect).

To identify breakpoint junctions, expected ecDNA structures were generated by Amplicon Architect (github.com/virajbdeshpande/AmpliconArchitect) from whole genome sequencing (WGS) data of primary HF3016 neurospheres (FIG. 2). Various types of circularized DNAs were identified then rearranged with different genomic fragments. Eight breakpoints from the expected circular DNA structures were selected at random for further analysis.

Figure 3A:
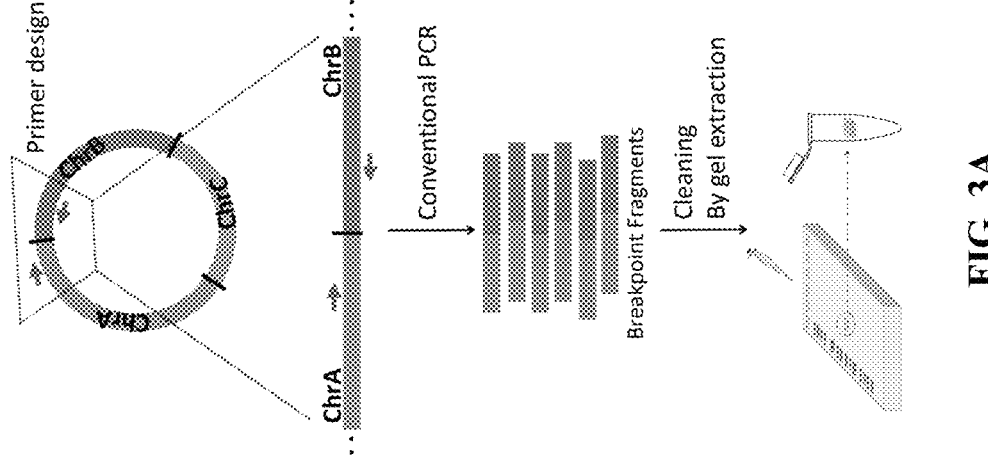
FIGS. 3A-3B. Breakpoint junction validation by breakpoint-PCR.
Figure 3B:
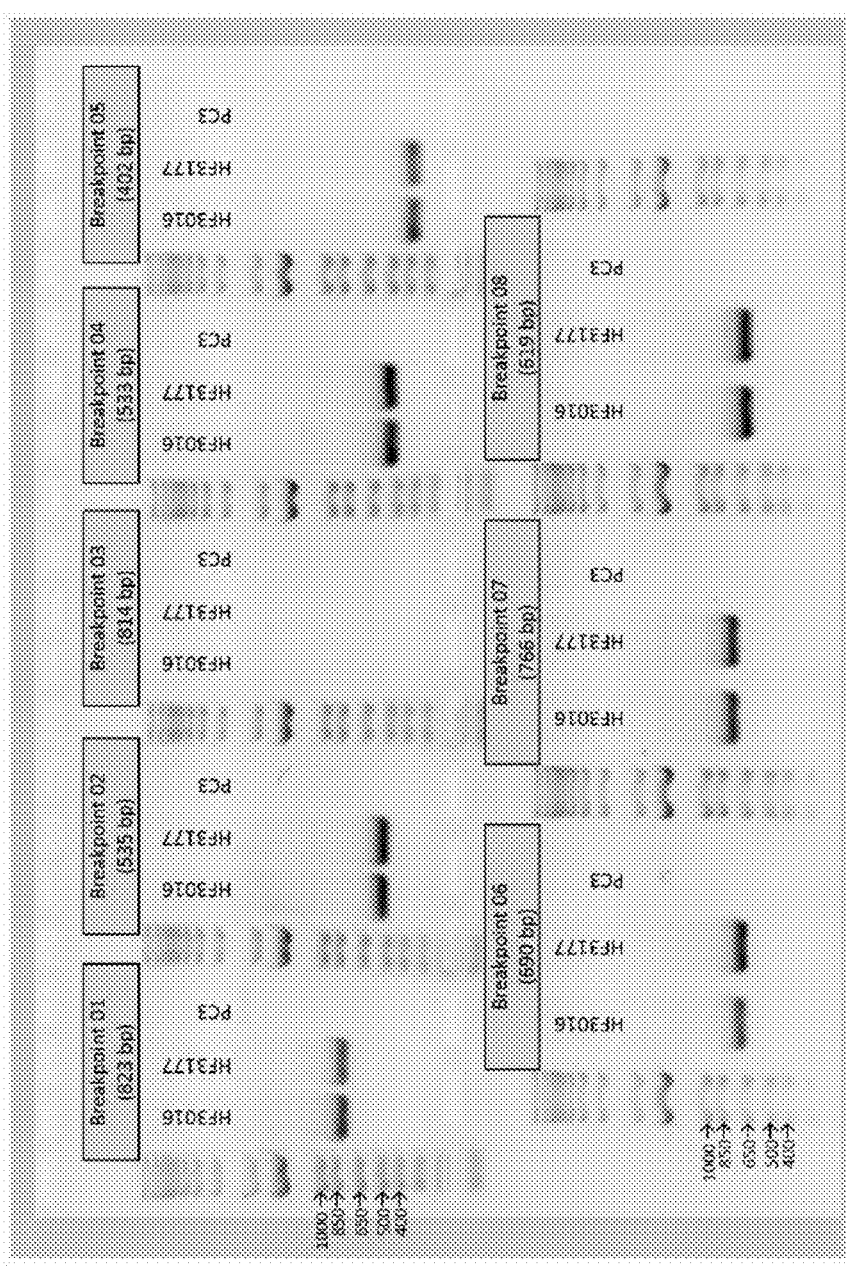

To confirm the breakpoint junctions, a breakpoint-specific PCR (BP-PCR) was conducted where each primer pair was designed to produce the final PCR product including each breakpoint region (FIG. 3A). To determine whether these breakpoints are shared between primary and recurrent tumors, BP-PCR was performed on the HF3016 primary neurosphere line, and the HF3177 line obtained from the recurrent tumor of the same patient. PC3, a prostate cancer cell line, was used as a negative control. Bands of the correct size, indicating the amplification of unique breakpoints were found in 7 of 8 BP-PCRs of HF3016 and HF3177, but not PC3, an expected outcome for a negative control (FIG. 3B). Additionally, Sanger Sequencing was performed on each PCR product purified from the gel to confirm the suspected sequence for each breakpoint (FIG. 3A).

Figure 4A:
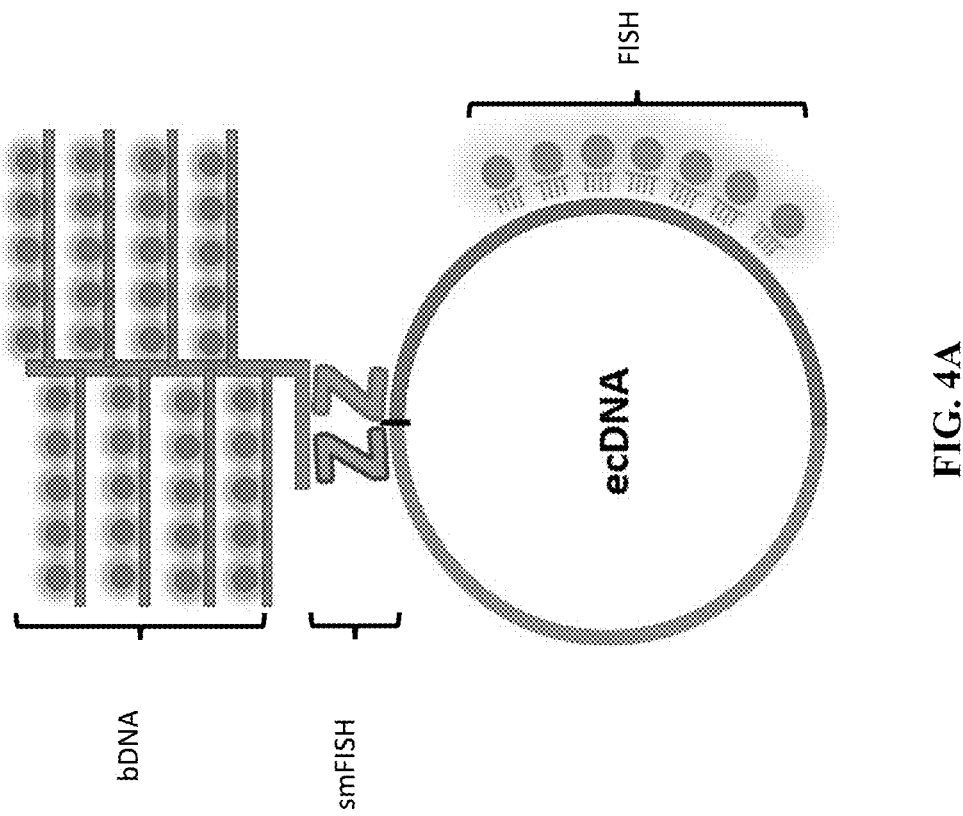
FIGS. 4A-4C. Breakpoint junction validation by breakpoint-FISH analysis.
Figure 4B:
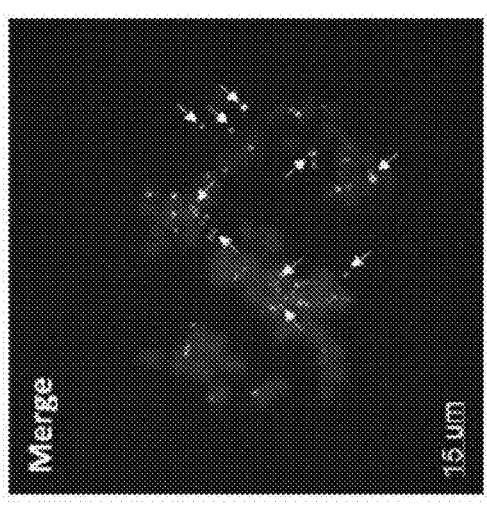
Figure 4B:
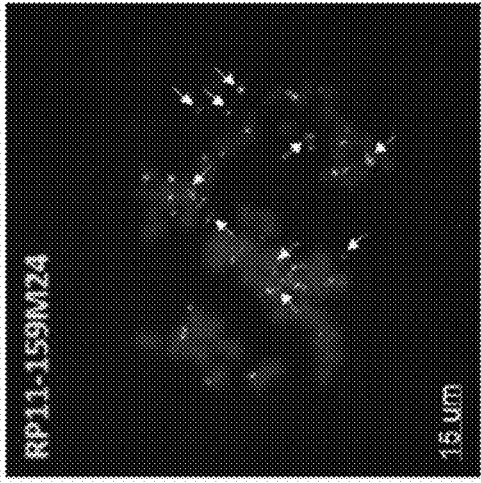
Figure 4C:
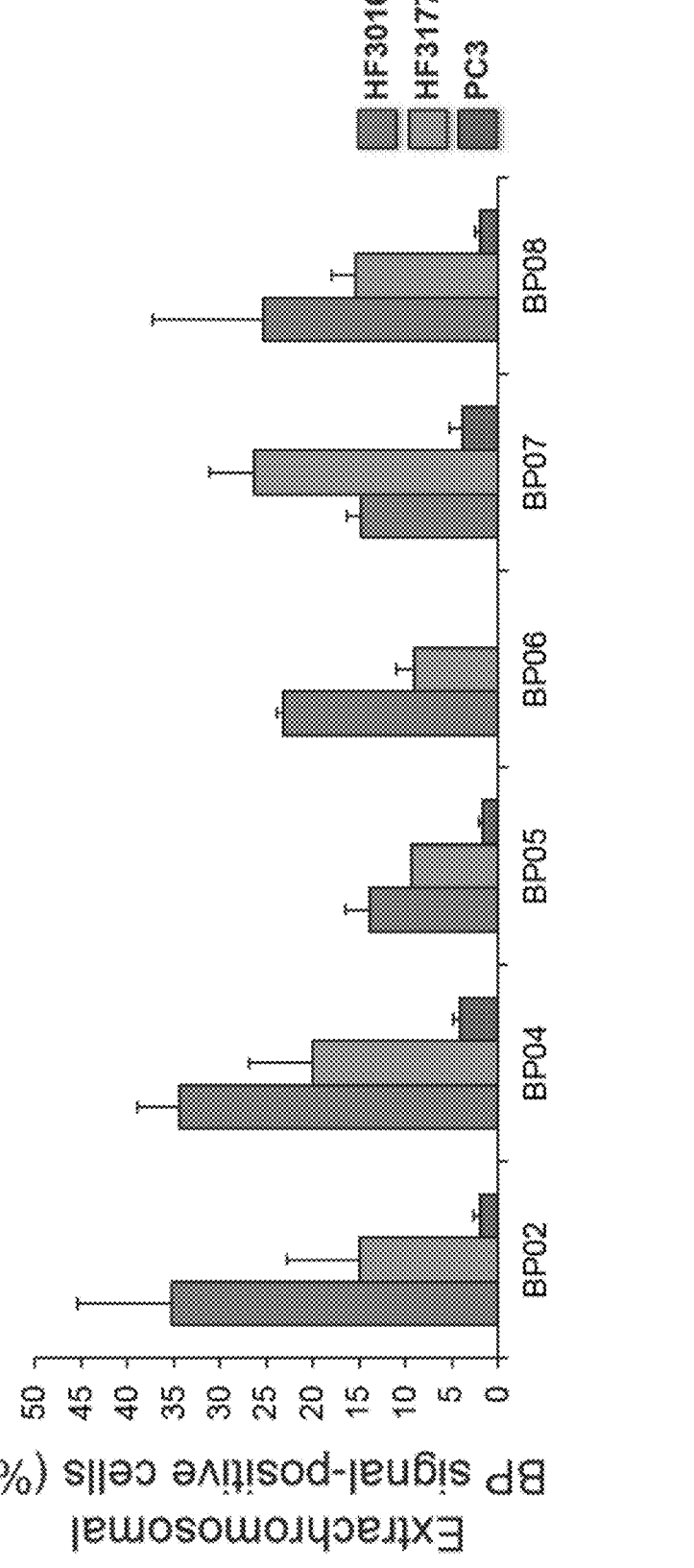

For additional validation BP-FISH was designed as a combination of single-molecule FISH and a branched-DNA technique to determine the location and amount of target breakpoint (FIG. 4A). Extracellular breakpoint signals, observed through confocal microscopy, showed that all breakpoints are presented on ecDNA (FIG. 4B). Further analysis was done by manually counting fluorescent signals (FIG. 4C).

Example 2: Targeting Efficiency Test of gRNA Using the Cell-Free System

Single guide RNA (gRNA) was designed to individually target six identified breakpoint junctions. A partial structure of ecDNA was generated that included junction regions confirmed through Sanger Sequencing results. These 20-nucleotide long target breakpoint junctions included nucleotides from both sides of the junction and were selected according to the availability of the protospacer adjacent motif (PAM) sequence which is essential for effective targeting using the CRISPR/Casilio system (FIG. 5). The specificity of each target breakpoint junction was scored by the CRISPOR program (crispor.tefor.net) (FIG. 5).

Figure 6A:
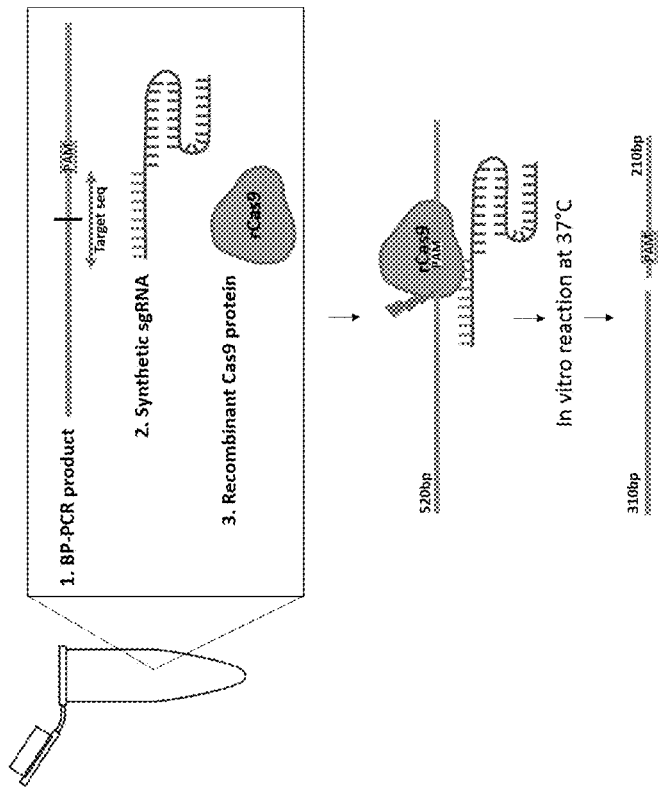
FIGS. 6A-6B. Cell-free targeting efficiency test.
Figure 6B:
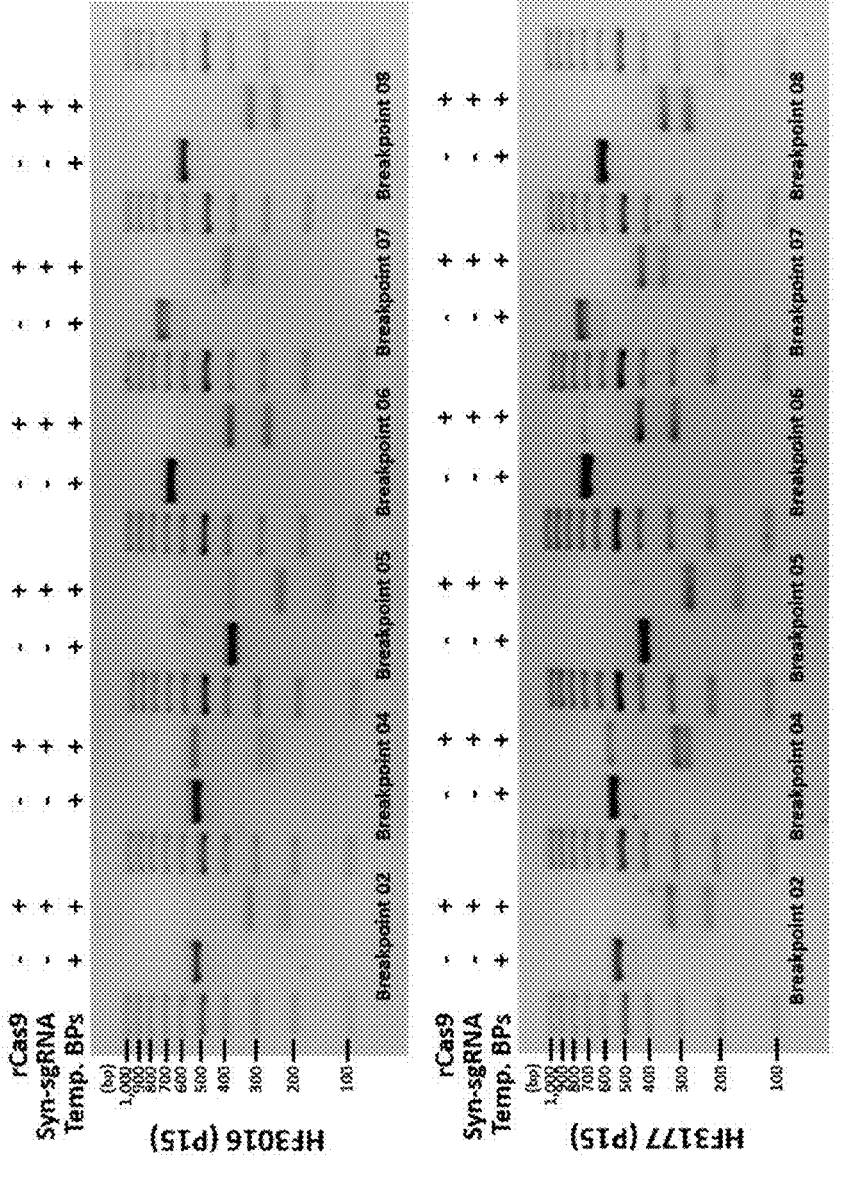

The cell-free test system (Guide-it™ gRNA In Vitro Transcription and Screening System, Takara Bio) was used to determine the targeting efficiency of the gRNA designed. This system measures the binding of gRNAs to target sequences (FIG. 6A). The DNA fragments obtained from the BP-PCR (FIG. 3) were used as template DNA. In vitro synthesized gRNAs for each breakpoint were incubated with the corresponding template DNA, as well as recombinant Cas9 at 37° C. After in vitro reaction, the targeting effect of each gRNA was observed by detecting the fragmented bands (FIG. 6B). This method was performed on all six gRNAs and each gRNA successfully targeted the corresponding breakpoint junction.

Example 3: Targeting Efficiency Test of EDTBv1

Figure 7A:
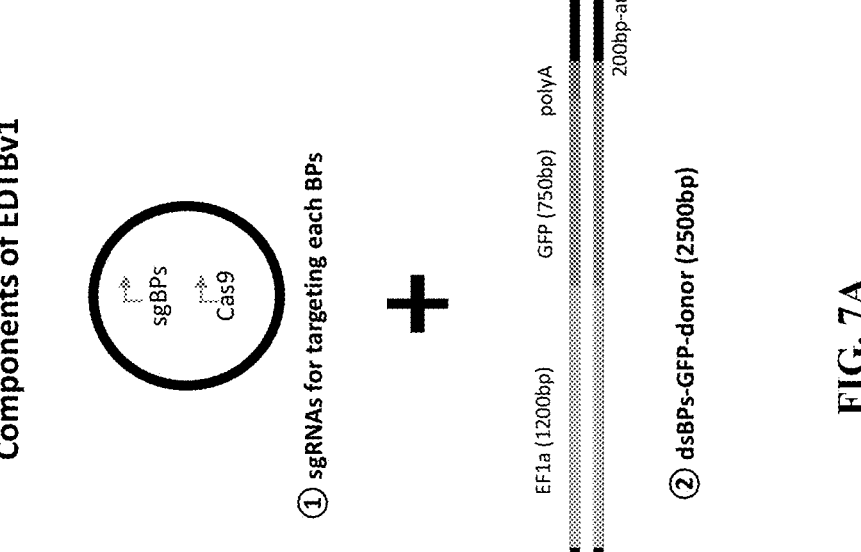
FIGS. 7A-7B. EDTBv1 components and transduction procedure.
Figure 7B:
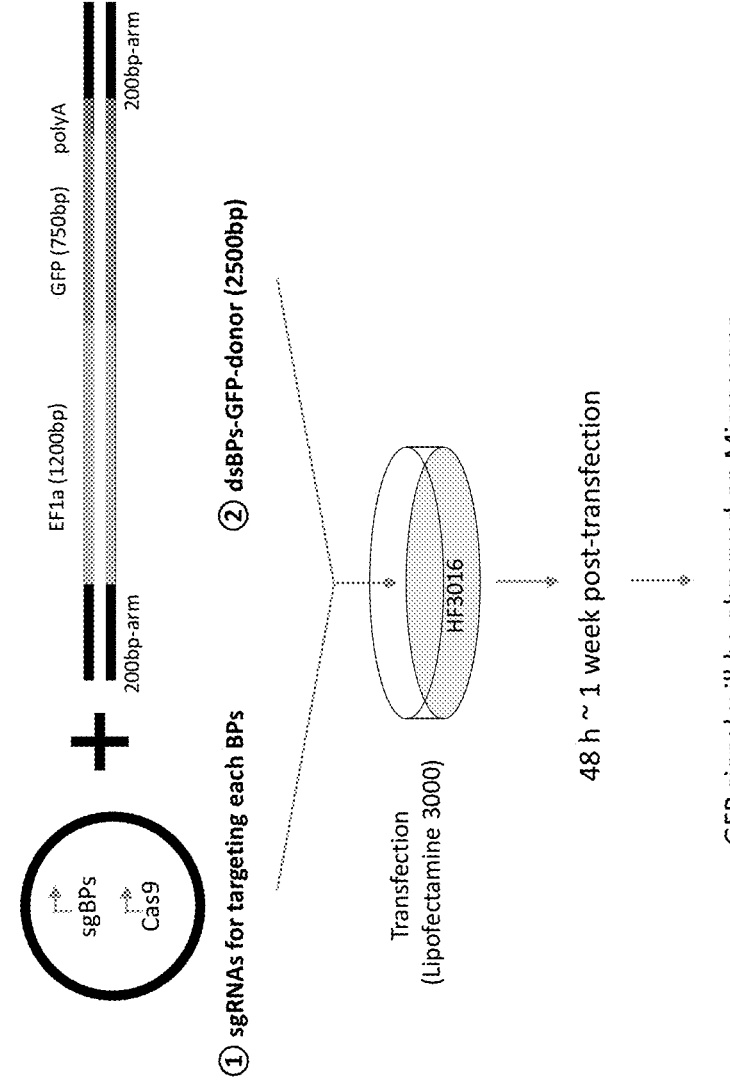

To develop EDTBv1, which will insert the GFP expression cassette into ecDNA through HDR system, the spacer sequences of each breakpoint have been cloned into a plasmid capable of producing gRNA and Cas9 at the same time. The donor DNA was designed with a promoter (EF1a), GFP sequence, polyA signal sequence, and the homology arms at both ends of the donor. The donor was designed to be double stranded, which is more stable than a single strand (FIG. 7A). The EDTBv1 components will be introduced into HF3016. The GFP signal will be observed microscopically to establish the optimal time point of GFP integration (FIG. 7B).

Example 4: Targeting Efficiency Test of EDTBv2

Figure 8B:
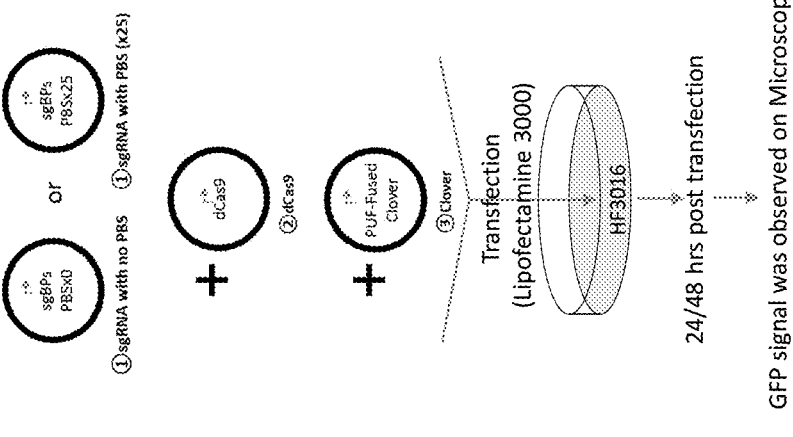
FIGS. 8A-8D. EDTBv2 components and transduction procedure.
Figure 8A:
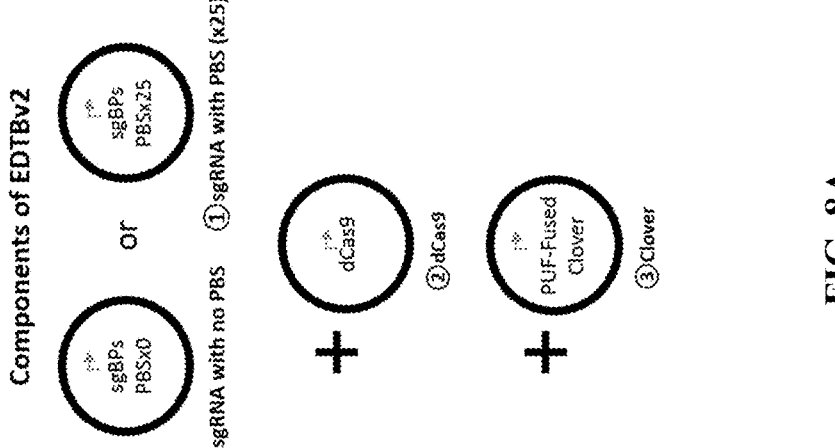
Figure 8C:
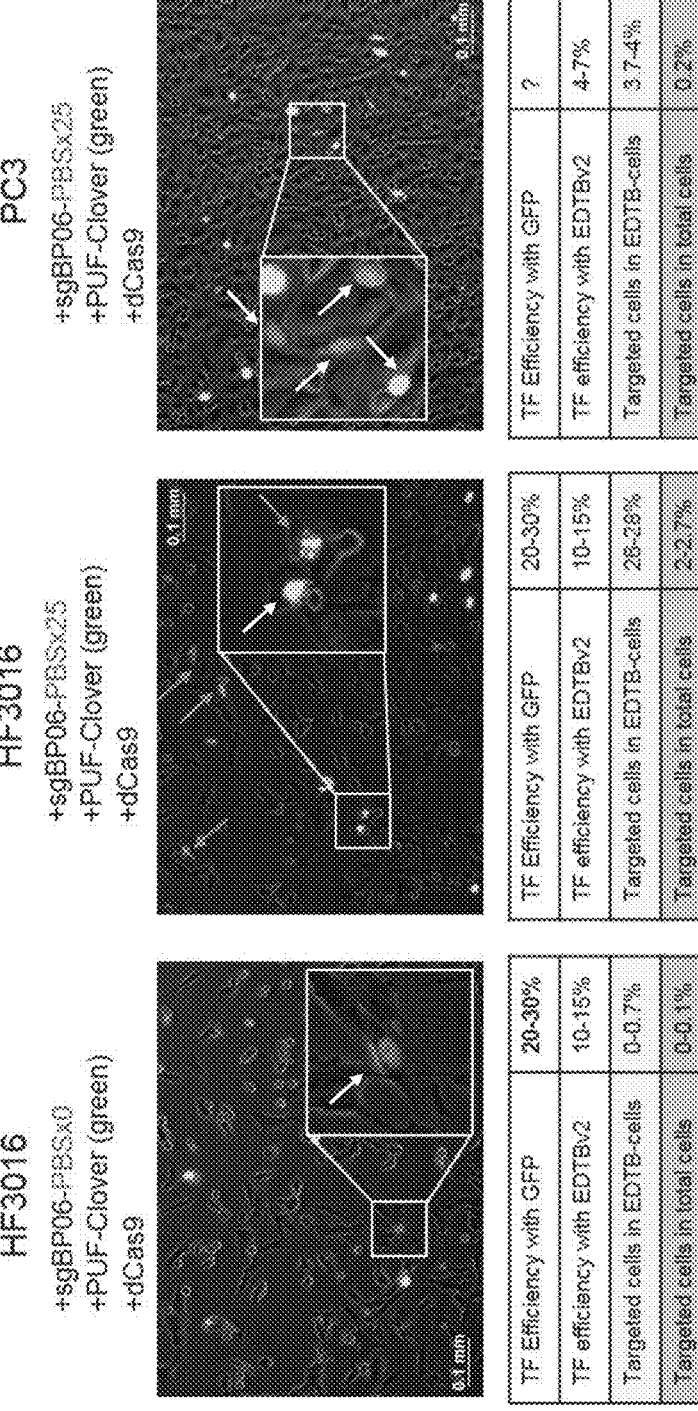
Figure 8D:
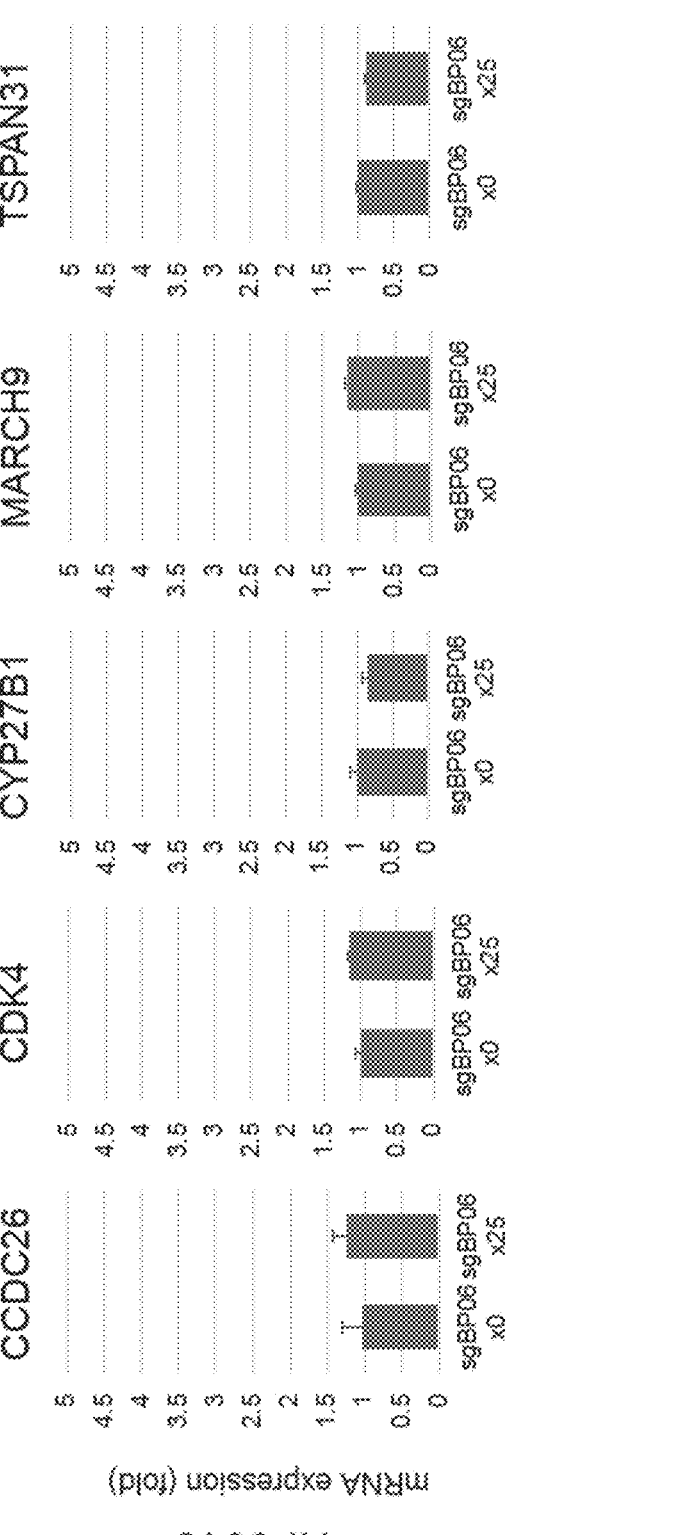
Figure 9A:
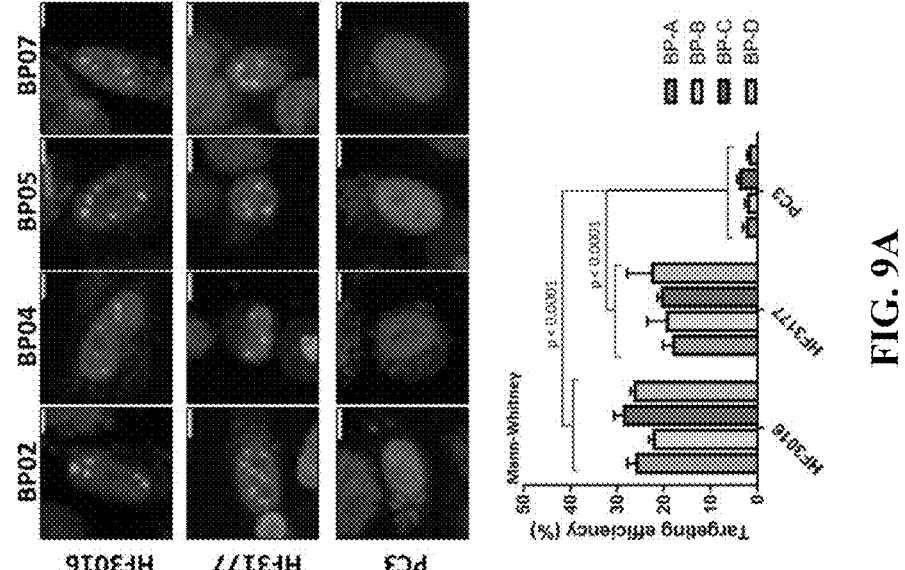
FIGS. 9A-9B. EDTBv2 targeting validation.
Figure 9B:
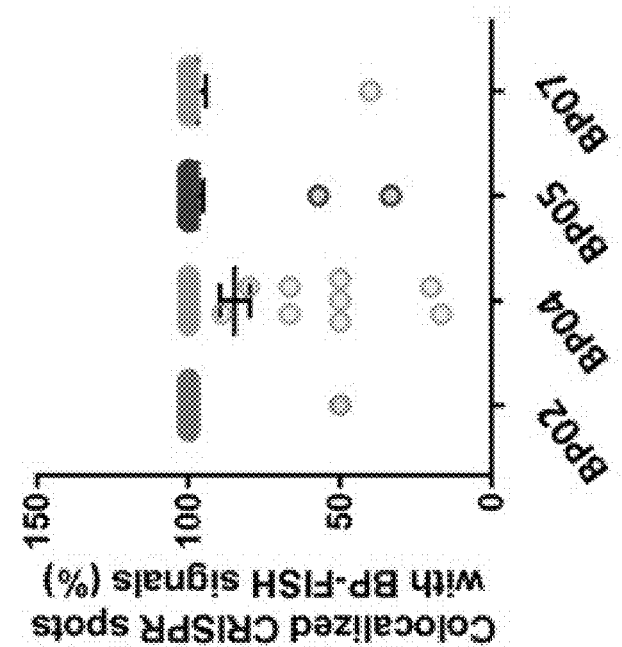
Figure 9B:
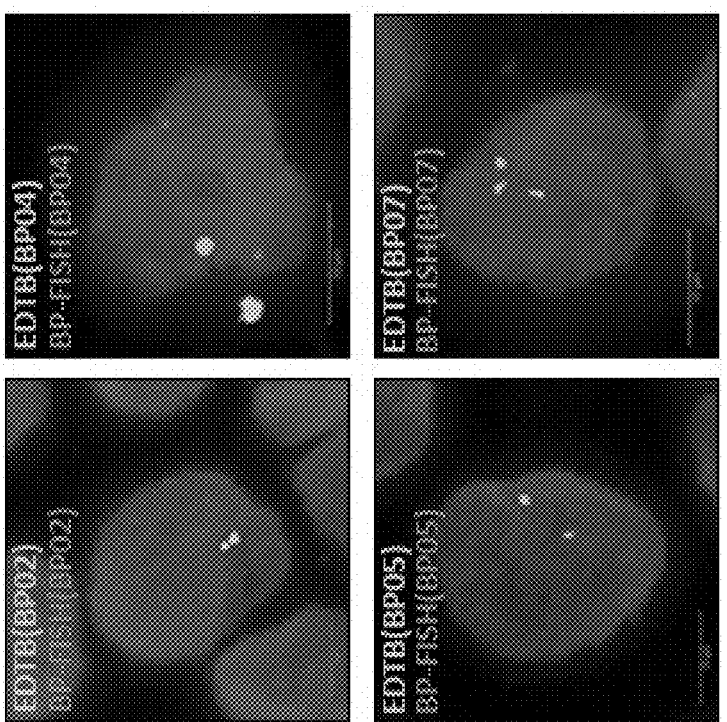

The component plasmids of EDTBv2 include: a modified gRNA which has multiple Pumilio/FBF (PUF) binding sites (PBS), a catalytically inactive Cas9 (dead Cas9 or dCas9), and PUF-fused Clover (Clover is one of the brightest fluorescent proteins and has very similar excitation and emission peak wavelength with GFP) (FIG. 8A). The spacer sequences of each breakpoint have been cloned into the gRNA plasmid. EDTBv2 components were introduced into HF3016 and PC3 (negative control) cells. The gRNA plasmid without PBS was used as a negative control. The Clover signal was observed microscopically ~24-48 hours after transfection (FIG. 8B). Targeting efficiency of EDTBv2 was first tested by targeting Breakpoint-06 (BP06). The cells harboring BP06 showed accumulated Clover signal at the specific location in their nucleus (FIG. 8C, red arrows) but the cells without BP06 showed broadly distributed clover signal across their nucleus (FIG. 8C, white arrows). The targeted cell (BP06-positive cell) population within the EDTBv2 transduced cells were 26-28% which corroborates the BP-FISH result (FIG. 4C, BP06). Additionally, qPCR was used to show whether EDTBv2 altered the expression level of BP06-related genes that are structurally involved in the same ecDNA (FIG. 8D) and found the BP06-related genes were not affected by EDTBv2. Then EDTBv2 components of each breakpoint (BP02, BP04, BP05, and BP07) were transfected into HF3016, HF3177 and PC3 (negative control) cells. The representative images displayed that HF3016 and HF3177, the breakpoint-expressing cells, showed plenty of the accumulated Clover signals indicating breakpoints of ecDNAs in their nucleus but not in the negative control cells (FIG. 9A, top panel). The mean targeting efficiency of this tool on HF3016 and HF3177 is 26% and 20.4% respectively with a slight off-target effect (2.7%) on PC3 (FIG. 9A, lower panel). The colocalized two-color signals of BP-FISH (red) and EDTBv2 (green) suggested that the signals derived from EDTBv2 are sufficiently indicating the specific breakpoint (FIG. 9B).

Example 5. Tracing ecDNA Dynamics in GSC ecDNA is likely not equally distributed to daughter cells and this unfair distribution may ultimately provide some of the genetic diversity of cancer. The extraordinary behavior of ecDNA signifies that ecDNA-positive cells may require different therapeutic approaches. For this reason, having information of ecDNA dynamics will further enable research aimed at better personalized therapies. In this Example, we will track ecDNA dynamics including their inheritance pattern, and horizontal transfer by using EDTB.

Figure 10A:
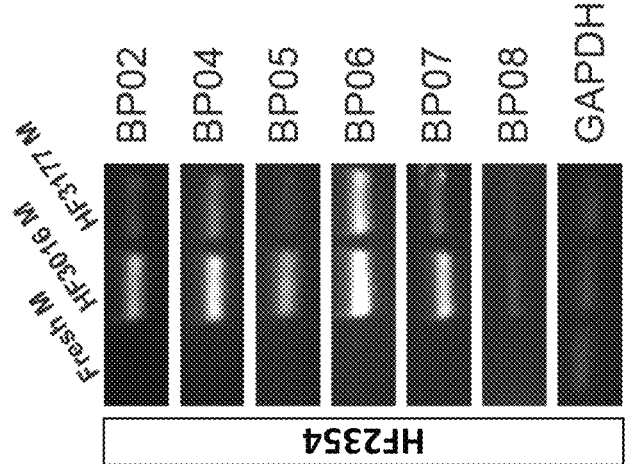
FIGS. 10A-10B. The evidence of horizontal ecDNA transfer between different neurosphere lines.
Figure 10B:
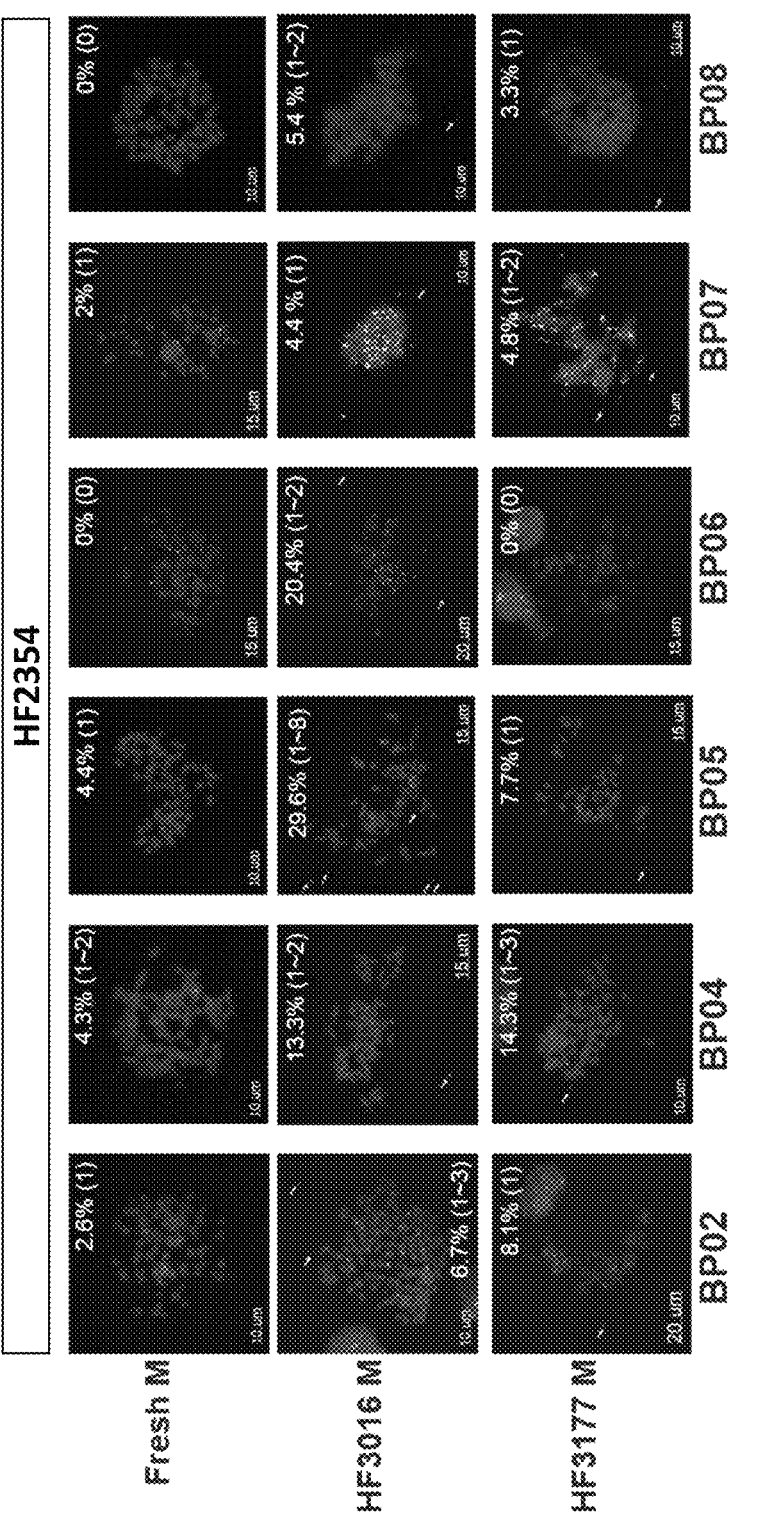

One question posed about ecDNA dynamics is whether horizontal gene transfer (HGT) could explain the dynamic behavior of ecDNA. Before applying the EDTB system, we wanted to see if ecDNA could be found in the cell medium, as a preliminary step toward identifying cell-cell transfer. Thus, we collected 3 days old cell media from HF3016 (primary) and HF3177 (recurrent) neurospheres. To eliminate the debris of donor cells, the cultured media were filtered through a 0.45-micrometer membrane which allows the passage extracellular vesicles, the potential carriers of ecDNA. Then, the collected media were added to potentially receptive cells, in this case HF2354, which are glioma neurosphere cells obtained from a different patient. FIG. 10A demonstrates that HF2354 in standard media lack the ecDNA breakpoints found in HF3016 and HF3177. HF2354 cells were incubated with filtered HF3016 or HF3177 media for 48 hrs, after which the HF2354 cells were thoroughly washed with DPBS and prepared for BP-PCR and BP-FISH analysis. Both methods confirmed the transfer of nearly all breakpoints tested into recipient cells. The BP-FISH results showed a significant population of breakpoint-positive cells were in metaphase (FIG. 10B). While the possibility of the transferred ecDNA being located outside of the nucleus was ruled out by the BP-FISH results, this result emphasizes the importance of studying ecDNA dynamics, as ecDNA could be a source of oncogenes and therapy-resistance genes.

Materials and Methods

Vectors and Plasmids

The Addgene #42230 vector (pX330-U6-Chimeric_BB-CBh-hSpCas9) was used to co-express Cas9 and gRNA for EDTBv1. The Addgene #71890 vector (pAC1373-pX-sgRNA-25×PBSa) and Addgene #71898 vector (pAC1394-pX-sgRNA-OxPBS) were used to express the gRNAs for EDTBv2. The Addgene #73169 vector (pAC1445-pmax-dCas9) was used to express dCas9 in cells for EDTBv2. The Addgene #73688 vector (pAC1446_pmax-Clover_PUFa) was used to express PUF-Clover in cells for EDTBv2.

Cloning

For the EDTBv1 system, guide sequences for each target were cloned into the Addgene #42230 vector using BbsI. For the EDTBv2, the guide sequences for each target were cloned into the Addgene #71898 and #71890 vectors using BbsI.

Cell Lines and Cell Culture

HF3016 and HF3177 neurospheres were cultured under neurosphere culture condtions (1% of N2 supplement, 0.5 mg/ml of BSA, 0.025 mg/ml of Gentamicin and 0.5% of Antibiotic/Antimycotic in 500 ml of DMEM/F12 medium) with growth factors (20 ng/ml of EGF and 20 ng/ml of FGFb). Neurosphere culture medium was changed twice weekly and each neurosphere line was passaged every 2 weeks. For dissociation and passaging, the medium containing the neurospheres was transferred to a 15 ml tube, centrifuged at 200×g for 3 minutes and the medium was removed. Add 10 ml Ca+2-, Mg+2-free DPBS and neurospheres were resuspended and incubated for 10 minutes at room temperature. Dissociated cells were resuspended in fresh neurosphere medium.

Transduction of Plasmids for gRNA, dCas9 Protein, and PUF-Fused Fluorescent Molecule Three different plasmids of EDTBv2 (Addgene numbers 71890 or 71898, 73169, and 73688) which are encode the gRNA, dCas9, and PUF-fused Clover, respectively, were co-transduced into neurospheres using Lipofectamine 3000 (Invitrogen, #L3000015). Generation and Statistical Analysis of Target Sequences The specificity of each gRNA target sequence was scored by the CRISPOR program (crispor.tefor.net). This score is a prediction of the degree to which a gRNA sequence for this target may lead to off-target effects in the genome. The score ranges from 0 to 100, with 100 being the most on-target effects. Preferable gRNAs have a specificity score of at least 50, and the specificity scores of all of the target sequences in this application were greater than 60.

DNA Isolation and PCR

Genomic DNA (gDNA) was isolated from neurospheres using a QIAamp DNA Mini kit (Qiagen, #51304) and 50 ng of each gDNA was used as a template DNA. The genomic region surrounding each breakpoint was amplified using AccuPrime Taq DNA Polymerase System (Invitrogen, #12339016). Primer pairs were designed to produce the PCR amplicons including the breakpoint junctions. Thermal cycling was carried out under the following conditions: 95° C. followed by 30 cycles of 30 sec at 95° C., 30 sec at 61° C., 1 min at 68° C.

Gel Purification for Sanger Sequencing

PCR amplicons were analyzed by agarose gel electrophoresis and purified from the gel using a Nucleospin Gel and PCR Clean-up kit (MACHEREY-NAGEL, #740609).

Breakpoint-Specific Fluorescence In Situ Hybridization

Metaphase neurosphere cells were prepared by adding 80 ng/ml of colcemid to arrest the cell cycle. The prepared metaphase neurosphere cells were fixed and plated on a slide. DNA FISH probe sets for each breakpoint junction were hybridized using the QuantiGene VeiwRNA miRNA ISH Cell Assay kit (Invitrogen, #QVC001) according to the modified method described therein. A probe set including custom-made probes targeting each breakpoint junction purchased from Invitrogen, and regular bacterial artificial chromosomes (BAC) probes targeting autosomal region purchased from Empire Genomics were used to detect breakpoint-specific fluorescence signal. The metaphase neurosphere slide was incubated for 5 min at 82° C. with denaturation buffer including a FISH probe set. The metaphase neurospheres were hybridized with a FISH probe set at 40° C. for overnight. Branched DNA (bDNA) methods were used to amplify the probe fluorescence according to the known procedures.

Confocal Microscopy

For the BP-FISH experiments (FIG. 4), the images were captured on an Andor Dragonfly Spinning Disk system with iXon camera. An oil-immersion objective (60×) was used to observe metaphase chromosome bodies. 405 nm, 488 nm, and 561 nm excitation lasers were used to detect chromosomes bodies, FISH probes, and bDNA-probes respectively.

For the efficiency test of EDTBv2 (FIG. 8), the images were captured on an inverted Nikon Eclipse Ti microscope with Andor Clara camera. A 10× objective was used to detect cell bodies. A FITC laser was used to detect the ecDNA signals. Cell morphology was captured using phase contrast and merged with ecDNA signals.

Image Analysis

For the BP-FISH experiment (FIG. 4), the images were processed using Imaris imaging software. The breakpoint signals were manually counted. For the efficiency test of EDTBv2 (FIG. 8), the images were processed using NIS-Elements imaging software. The total cell number and ecDNA signals were manually counted using ImageJ.

Targeting Efficiency Using Cell Free System

Guide-it Complete sgRNA Screening System (Takara Bio, #632636) was used to assess targeting efficiency. The PCR products obtained from BP-PCR were used as template DNA. sgRNAs were synthesized in vitro and purified via spin column. The cleavage reactions was performed by adding recombinant Cas9 and synthesized sgRNA to the template DNA. The cleavage efficiency was analyzed on an agarose gel.

qPCR and Statistical Analysis

Total RNA was extracted from neurospheres using All Prep DNA/RNA Mini kit (Qiagen, #80204). For the reverse transcript reaction, 1 μg of total RNA was used to synthesize cDNA using QuantiTech Reverse Transcription Kit (Qiagen, #205311). qPCR was performed to measure breakpoint-related gene expression levels using the PowerUp™ SYBR Green Master Mix (Life Technologies, #A24742). The reaction conditions were as follows: 1 cycle of 50° C. for 2 min and 95° C. for 2 min; 40 cycles of 95° C. for 15 sec, 57° C. for 15 sec and 72° C. for 1 min. The melt curve stage was as follows: 1 cycle of 95° C. for 15 sec, 60° C. for 1 min and 95° C. for 15 sec. The comparative CT (the delta delta CT) method was used to calculate the fold change in gene expression between the different groups. Gene expression data was analyzed using QuantStudio™ Real-Time PCR Software.

| SEQUENCES | | |
|---|---|---|
| Region | gRNA target sequence | gRNA targeting sequence |
| BP02 | TACTAAACCCTGATTATGAT (SEQ ID NO: 2) | UACUAAACCCUGAUUAUGAU (SEQ ID NO: 8) |
| BP04 | TGGCTCATCATGAGGCACTT (SEQ ID NO: 3) | UGGCUCAUCAUGAGGCACUU (SEQ ID NO: 9) |
| BP05 | AAGAGTGTCATTCCATCCTG (SEQ ID NO: 4) | AAGAGUGUCAUUCCAUCCUG (SEQ ID NO: 10) |
| BP06 | TTTGTGGCACTCTCCCAGGA (SEQ ID NO: 5) | UUUGUGGCACUCUCCCAGGA (SEQ ID NO: 11) |
| BP07 | ATATCTATACCTATTACACA (SEQ ID NO: 6) | AUAUCUAUACCUAUUACACA (SEQ ID NO: 12) |
| BP08 | TGTTTCCTACTGAAGAATTG (SEQ ID NO: 7) | UGUUUCCUACUGAAGAAUUG (SEQ ID NO: 13) |

All references, patents and patent applications disclosed herein are incorporated by reference with respect to the subject matter for which each is cited, which in some cases may encompass the entirety of the document.

The indefinite articles "a" and "an," as used herein the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method capable of detecting a single extrachromosomal deoxyribonucleic acid (ecDNA) in a cell, the method comprising binding at most one non-repetitive breakpoint junction sequence on the ecDNA with a catalytically-inactive RNA-guided nuclease complexed with a guide RNA (gRNA) targeting the non-repetitive breakpoint junction sequence and linked to a multiplicity of detectable molecules that are sufficient to be detected.

2. The method of claim 1, wherein the cell is a cancer cell.

3. The method of claim 2, wherein the cancer cell is a glioblastoma cell, a melanoma cell, a sarcoma cell, a bladder cancer cell, or an esophageal cancer cell.

4. The method of claim 1, wherein the gRNA comprises (a) a targeting sequence that is complementary to the non-repetitive breakpoint junction, (b) a RNA-guided nuclease-binding sequence, and (c) multiple Pumilio-FBF domain binding sequences (PBS).

5. The method of claim 4, wherein the multiple detectable molecules are linked to the gRNA via multiple Pumilio-FBF (PUF) domains, and wherein the multiple PUF domains bind to the PBS on the gRNA.

6. The method of claim 1, wherein the catalytically-inactive RNA-guided nuclease is dCas9.

7. The method of claim 1, wherein the detectable molecules are fluorescent proteins.

8. The method of claim 1, wherein the detecting comprises imaging the detectable molecules of the cell.

9. The method of claim 1, further comprising introducing into the cell:

(a) the catalytically-inactive RNA-guided nuclease or a nucleic acid encoding the catalytically-inactive RNA-guided nuclease, (b) the gRNA comprising:

(i) a targeting sequence that is complementary to the non-repetitive breakpoint junction, (ii) a RNA-guided nuclease-binding sequence, and (ii) Pumilio-FBF domain binding sequences (PBS), and (c) one or more Pumilio-FBF (PUF) domains linked to the multiplicity of detectable molecules, wherein the one or more PUF domains bind to the PBS.

\* \* \* \* \*